(12) United States Patent
Fukami et al.

(10) Patent No.: US 7,602,487 B2
(45) Date of Patent: Oct. 13, 2009

(54) SURFACE INSPECTION APPARATUS AND SURFACE INSPECTION HEAD APPARATUS

(75) Inventors: Yukiko Fukami, Kanagawa (JP); Hideo Mori, Kanagawa (JP)

(73) Assignees: Kirin Techno-System Corporation, Kanagawa (JP); KTS Optics Corporation, Kanagawa (JP)

( * ) Notice: Subject to any disclaimer, the term of this patent is extended or adjusted under 35 U.S.C. 154(b) by 80 days.

(21) Appl. No.: 11/748,768

(22) Filed: May 15, 2007

(65) Prior Publication Data

US 2008/0079933 A1    Apr. 3, 2008

(30) Foreign Application Priority Data

| May 16, 2006 | (JP) | 2006-136809 |
| May 23, 2006 | (JP) | 2006-143193 |
| May 23, 2006 | (JP) | 2006-143420 |

(51) Int. Cl.
    *G01N 21/00* (2006.01)
(52) U.S. Cl. .................. 356/241.1; 356/237.1
(58) Field of Classification Search ... 356/237.1–241.6, 356/426–431, 600–640
    See application file for complete search history.

(56) References Cited

U.S. PATENT DOCUMENTS

| 3,679,307 | A | * | 7/1972 | Zoot et al. .................. 356/3.06 |
| 3,918,438 | A | * | 11/1975 | Hayamizu et al. ........... 600/168 |
| 4,243,882 | A | * | 1/1981 | Yasujima et al. ....... 250/339.06 |
| 4,255,762 | A | * | 3/1981 | Takeyasu et al. .............. 348/84 |
| 4,583,858 | A | * | 4/1986 | Lebling et al. .............. 356/402 |
| 4,615,333 | A | * | 10/1986 | Taguchi ....................... 600/171 |
| 4,732,474 | A | * | 3/1988 | Chikama .................. 356/237.1 |
| 4,771,415 | A | * | 9/1988 | Taki ....................... 369/112.27 |
| 5,416,638 | A | * | 5/1995 | Broome ...................... 359/656 |
| 6,193,666 | B1 | * | 2/2001 | Ouchi ........................ 600/459 |
| 6,320,652 | B1 | * | 11/2001 | Morimoto et al. ........... 356/124 |
| 6,638,216 | B1 | * | 10/2003 | Durell ......................... 600/173 |
| 6,689,947 | B2 | * | 2/2004 | Ludwig ....................... 84/721 |
| 6,936,004 | B2 | * | 8/2005 | Utsui .......................... 600/182 |
| 2002/0097400 | A1 | * | 7/2002 | Jung et al. .................. 356/419 |
| 2004/0036874 | A1 | * | 2/2004 | Kramer ...................... 356/342 |

FOREIGN PATENT DOCUMENTS

| JP | 50-159355 |   | 12/1975 |
| JP | 58-105517 | U | 7/1983 |
| JP | 59-065708 | A | 4/1984 |
| JP | 63-153456 | A | 6/1988 |
| JP | 64-054304 | A | 3/1989 |
| JP | 01-097809 | A | 4/1989 |
| JP | 3-25144 | U | 3/1991 |
| JP | 06-180291 | A | 6/1994 |
| JP | 06-235696 | A | 8/1994 |
| JP | 08-304299 | A | 11/1996 |
| JP | 11-281582 | A | 10/1999 |

(Continued)

*Primary Examiner*—Gregory J Toatley, Jr.
*Assistant Examiner*—Jarreas C. Underwood
(74) *Attorney, Agent, or Firm*—Darby & Darby

(57) ABSTRACT

A surface inspection apparatus has a detection unit that irradiates an inner circumferential surface of an inspection object with inspection light from a laser diode through a light projecting fiber, and detects the intensity of the reflected light of that inspection light. The detection unit comprises a first light receiving fiber group, which is disposed at the circumference of the light projecting fiber, a second light receiving fiber group, which is disposed further on the outer side thereof, and photodetectors, which are connected to each of the fiber groups.

2 Claims, 10 Drawing Sheets

FOREIGN PATENT DOCUMENTS

| JP | 2002-156332 A | 5/2002 |
| JP | 2003-130806 A | 5/2003 |
| JP | 2005-140679 A | 6/2005 |
| JP | 2005-164398 A | 6/2005 |

* cited by examiner

SURFACE INSPECTION APPARATUS AND SURFACE INSPECTION HEAD APPARATUS

BACKGROUND OF THE INVENTION

1. Field of the Invention

The present invention relates to: a surface inspection apparatus that detects the intensity of reflected light of inspection light irradiated on a surface of an inspection object and, based on the detected intensity of the reflected light, inspects the surface of the inspection object; a surface inspection apparatus that inspects for defects, such as foreign matter and scratches, that are present on the inner circumferential surface of a cylindrical body, which is the inspection object; or a surface inspection head apparatus that inspects the surface of the inspection object.

2. Related Art

A known example of an apparatus that inspects the inner circumferential surface of a cylindrical inspection object is a surface inspection apparatus (e.g., refer to JPA H11-281582) that feeds a shaft shaped inspection head in an axial direction while rotating it therearound in order to insert it inside of the inspection object, irradiates the inspection object with inspection light from the outer circumference of that inspection head, successively scans the inner circumferential surface of the inspection object from one end to the other in its axial directions, receives light reflected by the inspection object through the inspection head in accordance with that scan, and, based on the intensity of that received reflected light, determines the state of the inspection object, e.g., whether any defects and the like are present. In addition, among surface inspection apparatuses of the type discussed above, there is one that can inspect the inner circumferential surface of a cylindrical body, such as a cylinder liner or a cylinder bore of an internal combustion engine, by projecting inspection light thereto, inserting a rod shaped inspection head, which is configured so that it receives light reflected by the inner circumferential surface, inside the cylindrical body, and then advancing and retracting the inspection head, relative to the cylindrical body, in its axial directions while rotating it around its axis, which extends in the longitudinal direction. Such an inspection apparatus generates a two dimensional image, based on the intensity of the reflected light, that corresponds to the inner circumferential surface, and then determines whether there are any defects on the inner circumferential surface based on the presence of dark areas in that two dimensional image.

In addition, with the surface inspection apparatus discussed above, a head apparatus, which is provided with optical path modifying members such as a mirror and a prism, is built into the interior of a head tube, wherein an opening is formed so that inspection light can pass therethrough to the outer circumference. With this head apparatus, the optical path of the inspection light is changed by the optical path modifying member so that it leads to the opening of the head tube, the reflected light of the light that emerges from that opening and impinges the surface of the inspection object enters the head tube from the opening, and the reflected light optical path is modified by the optical path modifying members so that it goes in the reverse direction of the inspection light, and thereby the light needed to inspect the surface of the inspection object for scratches, foreign matter, and the like is guided from the head tube to a light receiving part of the surface inspection apparatus. Rotating the head tube makes it possible to scan the inspection light over the entire circumference of the inner circumferential surface of a cylindrical inspection object in the circumferential direction. To protect the interior of the head tube from contamination, a protective window member is provided to the opening of the head tube so that the front surface and the rear surface of the protective window member are orthogonal to the optical path of the inspection light.

The surface inspection apparatus discussed above comprises a detecting means that is configured so that a plurality of light receiving fibers, which receive reflected light, are adjoined around a light projecting fiber, which projects inspection light, and so that these optical fibers are held by a fiber holding tube. With this detecting means, the positional relationship between the light projecting fiber and the light receiving fibers, e.g., the distance therebetween, is fixed, and therefore the sensitivity characteristic of the detecting means with respect to changes in the properties of the reflected light, such as its direction or intensity, is also fixed. Because the type of defect present in the inspection object characterizes the property of the reflected light, the position and the like of the light receiving fibers in a conventional surface inspection apparatus are set so that the detecting means is provided with a sensitivity characteristic that can sense the defects for which the inspection object is to be inspected.

Thus, with a conventional surface inspection apparatus, the sensitivity characteristic of the detecting means is fixed so that it is possible to sense the defect to be detected, which is a problem because if, for example, there is a change in the type of defect to be detected, then that defect cannot be adequately sensed; in addition, if locations that are to be distinguished from defects are newly set, then those locations will be mistakenly detected as defects.

In addition, if the surface inspection apparatus discussed above is used to inspect the inner circumferential surface of a cylindrical body, then the rotational axis of the inspection head and the center line of the cylindrical body must be made to coincide. As long as they coincide, the inspection head and the inner circumferential surface of the cylindrical body will always oppose one another, regardless of the rotational position of the inspection head, which makes it possible to receive reflected light of the same intensity provided that the intensity of the inspection light is constant and the properties of the inner circumferential surface are uniform. However, if the rotational axis of the inspection head and the center line of the cylindrical body do not coincide, then the angle of incidence of the inspection light will vary with the rotational position of the inspection head, which will change the intensity of the reflected light even if the properties of the inner circumferential surface are uniform.

In that case, with every rotation of the inspection head, there are two occasions when the inspection head and the inner circumferential surface oppose one another, and the angle of incidence varies gradually at times when they are not opposed, and therefore the intensity of the reflected light fluctuates. Consequently, when a two dimensional image is generated that has a density that is in accordance with the intensity of the reflected light, that two dimensional image is brightest at the position where the inspection head and the inner circumferential surface oppose one another, and is relatively darker elsewhere with a density (brightness and darkness) that varies periodically. If by chance there is a dark area, which corresponds to a defect, present in the relatively bright portion of the two dimensional image, then there will be no error in determining that it is a defect; however, if that dark area is present in a relatively dark portion, then the contrast around the dark part will be low, which increases the possibility of an error in determining that it is a defect.

In addition, if the protective window member is provided to the opening in the head apparatus discussed above, then, when the inspection light passes through the protective window member and emerges on the outer side of the head tube, the inspection light will be reflected by the front surface and the rear surface of the protective window member. This reflected light will return in a direction that is the reverse of that of the inspection light because of the optical path modifying members, and consequently the light reflected by the inspection object and the light reflected by the protective window member will be superimposed with the light detected by the surface inspection apparatus, which hinders the improvement of sensitivity.

SUMMARY OF THE INVENTION

It is an object of the present invention to provide a surface inspection apparatus that can produce a variety of sensitivity characteristics in accordance with, for example, the type of defect. It is another object of the present invention to provide a surface inspection apparatus that can obtain a two dimensional image without periodic density variation, even if the rotational axis of an inspection head and the center line of a cylindrical body, which is the inspection object, do not strictly coincide. It is yet another object of the present invention to provide a surface inspection head apparatus that is capable of separating the reflected light of the inspection light, which was reflected by the inspection object, from the light reflected by a protective window member, and guiding the former to an inspection apparatus.

The abovementioned problems are solved by a surface inspection apparatus according to a first aspect of the invention that has: a detecting means that irradiates a surface of an inspection object with inspection light from a light source through a light projecting fiber, and detects the intensity of reflected light of that inspection light; and that inspects the surface of the inspection object based on the detection result of the detecting means, wherein the detecting means comprises: a first light receiving fiber group that comprises a plurality of light receiving fibers, which is disposed at the circumference of the light projecting fiber and can guide the reflected light; a second light receiving fiber group that comprises a plurality of light receiving fibers, which is disposed on the outer side of the first light receiving fiber group viewed from the light projecting fiber and that can guide the reflected light; a first photoelectric converting means that outputs a signal in accordance with the intensity of the reflected light guided by the first light receiving fiber group; and a second photoelectric converting means that outputs a signal in accordance with the intensity of the reflected light guided by the second light receiving fiber group.

According to this surface inspection apparatus as discussed above, a second light receiving fiber group is disposed on the outer side of the first light receiving fiber group, and each of these fiber groups has a different positional relationship with the light projecting fiber. Consequently a single detecting means has a plurality of sensitivity characteristics that are different from one another. Accordingly, it is possible to produce a variety of sensitivity characteristics by appropriately using the signal of the first photoelectric converting means and the signal of the second photoelectric converting means in accordance with the type of the defect to be detected, or by combining these signals.

The first aspect of the invention may further comprise: a composite processing means that, based on a prescribed arithmetic rule, combines a first signal, which is output from the first photoelectric converting means, and a second signal, which is output from the second photoelectric converting means; and an arithmetic rule setting means that sets the prescribed arithmetic rule so that the sensitivity of the detecting means has a prescribed sensitivity characteristic. There are no limitations to the rules that are set by the arithmetic rule setting means. In addition, a plurality of types of arithmetic rules may be held in advance by the arithmetic rule setting means, and an appropriate arithmetic rule may be selected therefrom. For example, setting an arithmetic rule that simply adds the first signal and the second signal makes it possible to obtain a sensitivity characteristic that is substantially equivalent to the case wherein a single light receiving fiber group is provided that has a light receiving surface area that is the sum of the light receiving surface areas of those fiber groups, i.e., a case wherein the diameter of each of the light receiving fibers is enlarged.

Incidentally, if the inspection object is a casting and the surface to be inspected has undergone a cutting process, then it is required to detect any blow hole that appears in the surface of the casting as a defect and, simultaneously, to distinguish a blow hole, which is a defect, from a slight hollow formed in the surface by the cutting process. If a blow hole is present in the surface, then even if the inspection light irradiates the blow hole, it hardly reflects and, consequently, the intensity of the reflected light decreases. Moreover, the hollow formed in the surface changes the direction of the reflected light. Consequently, if the detecting means is sensitive to angular change in the reflected light, i.e., if the sensitivity characteristic related to the angular range of the reflected light has a narrow permissible range, then there are cases wherein the detecting means cannot receive the light that is reflected by the hollow of the surface. Thereby, the intensity of the received reflected light decreases and it becomes difficult to distinguish a blow hole from a hollow.

Accordingly, in the first aspect of the invention, the arithmetic rule setting means may set the prescribed arithmetic rule so that the sensitivity of the detecting means, which relates to the angular change of the light reflected by the surface of the inspection object, has a substantially flat sensitivity characteristic with respect to an angular change within a prescribed range. In this case, if the prescribed range is set so that it corresponds to the width of the angular change in the light reflected by the hollow, then the sensitivity characteristic within that range is substantially flat, and therefore the light reflected by the hollow can be received at an intensity that is equal to that of the light reflected by a surface that does not have a hollow. Accordingly, the blow hole and the hollow are clearly distinguished, which improves inspection accuracy.

The sensitivity characteristics of the first and second light receiving fiber groups in relation to angular change in the reflected light depend on their physical configurations such as the spacing between the optical fiber groups, the distance between the light projecting fiber and each fiber group, and the diameters of the light receiving fibers that constitute each of these fiber groups. Accordingly, the arithmetic rule needed to obtain such a flat sensitivity characteristic is appropriately set by taking into account the sensitivity characteristic of the first light receiving fiber group and the sensitivity characteristic of the second light receiving fiber group in relation to angular change in the reflected light. For example, the arithmetic rule setting means may set an arithmetic rule that adds the first signal to the product of the second signal and a prescribed value as the prescribed arithmetic rule. Such an arithmetic rule can also obtain a substantially flat sensitivity characteristic.

Incidentally, if the surface of the inspection object has undergone a cutting process, then a chip from that cutting process may adhere to the surface and it is required to detect the presence of that chip as a defect. If the inspection light irradiated on the chip barely reflects, or if the direction of the reflected light greatly deviates, then the intensity of the received reflected light decreases, which makes it possible to detect the chip. However, because the chip does not have a uniform shape, there is a risk that the presence of the chip will be overlooked if the inspection light irradiated on the chip reflects in a manner that is similar to a normal surface.

Accordingly, in the first aspect of the invention, the arithmetic rule setting means may set the prescribed arithmetic rule so that the sensitivity of the detecting means, which relates to a change in the distance of the inspection object to a reflection position, has a sensitivity characteristic that has a negative peak when the reflection position becomes closer by a prescribed distance. According to this aspect, setting the prescribed distance to, for example, the average dimension of the chip makes it possible to detect the chip because the presence of a chip causes the intensity of the received reflected light to take on a negative value, which reduces the risk that the presence of a chip will be overlooked. Because the arithmetic rule needed to obtain such a sensitivity characteristic depends on the physical configuration of the detecting means, as discussed above, it is set appropriately by taking into account the sensitivity characteristic of the first light receiving fiber group in relation to changes in the distance of the inspection object to the reflection position, as well as the sensitivity characteristic of the second light receiving fiber group. For example, the arithmetic rule setting means may set an arithmetic rule that subtracts the second signal from the first signal as the prescribed arithmetic rule. Even with such an arithmetic rule, it is possible to obtain a sensitivity characteristic that has a negative peak for the case wherein the reflection position becomes closer a prescribed distance.

The first aspect of the invention may be configured as an apparatus that inspects a planar surface of the inspection object, or as an apparatus that inspects a nonplanar surface of the inspection object. For example, a cylindrically shaped inner circumferential surface may be provided as the surface of the inspection object; and the detecting means may irradiate the inspection light from an outer circumference of a shaft shaped inspection head toward the cylindrical body inner circumferential surface; further comprising: a linear driving means that moves the inspection head in the axial directions; and a rotary driving means that rotates the inspection head around its axis.

The abovementioned problems are solved by a surface inspection apparatus according to a second aspect of the invention that comprises: a light source that emits inspection light; an inspection head that is inserted inside a cylindrical body, which is an inspection object, that, while rotating around an axis of the cylindrical body and moving in the axial directions, projects the inspection light emitted from the light source to an inner circumferential surface of the cylindrical body and receives the light reflected thereby; and a photoelectric converting means that outputs a signal in accordance with the intensity of the reflected light received by the inspection head; and that generates a two dimensional image that corresponds to the inner circumferential surface based on the signal output by the photoelectric converting means; further comprising: a signal processing means that extracts frequency components, which correspond to fluctuations in the intensity of the reflected light caused by a deviation between the axis and a center line of the cylindrical body, from the signal output by the photoelectric converting means; and a light source controlling means that controls the light source so that the intensity of the inspection light emitted from the light source varies with the differential between a prescribed reference value and the frequency components extracted by the signal processing means.

According to this inspection apparatus, the signal processing means extracts frequency components that corresponds to fluctuations in the intensity of the reflected light caused by a deviation between the rotational axis of the inspection head and the center line of the cylindrical body. Furthermore, because the light source controlling means controls the intensity of the inspection light in accordance with the differential between frequency components extracted by the signal processing means and the prescribed reference value, it is possible to eliminate fluctuations in the intensity of the reflected light. Thereby, it is possible to obtain a two dimensional image without any periodic density variation—even if the rotational axis of the inspection head and the center line of the cylindrical body, which is the inspection object, do not precisely coincide.

In the second aspect of the invention, the light source controlling means may control the light source so that the intensity of the inspection light emitted from the light source is greater when the differential between the reference value and the frequency components is large than when it is small. Thereby, fluctuations in the intensity of the reflected light can be eliminated reliably.

In the second aspect of the invention, the signal processing means may be configured so that it extracts frequency components within a prescribed range that includes frequency components that correspond to the fluctuations and does not include frequency components that correspond to a defect of the inner circumferential surface. In this case, appropriately setting the prescribed range makes it possible to generate a more uniform two dimensional image because it is possible to eliminate not only the fluctuations caused by a deviation between the rotational axis and the center line, but also changes in the intensity of the reflected light caused by other factors that can't be considered defects, e.g., surface roughness of the inner circumferential surface. In addition, because the prescribed range does not include frequency components that correspond to defects, the problem does not arise wherein a change in the intensity of the reflected light that corresponds to a defect is eliminated.

The abovementioned problems are solved by a surface inspection head apparatus according to a third aspect of the invention that comprises: a head tube wherein an opening is formed at its outer circumference; a protective window member, which is provided in the opening; and an optical path modifying means, which is provided inside the head tube, that modifies the optical path of inspection light that enters the head tube in an axial direction so that it leads toward the protective window member and modifies the optical path of the light of the inspection light reflected by an inspection object surface so that it leads along an axial direction of the head tube in a direction that is the reverse of the inspection light; wherein the normal line direction of at least one of the front surface and the rear surface of the protective window member is inclined in the direction in which the inspection light impinges the protective window member.

The normal line direction of at least one of the front surface and the rear surface of the protective window member is inclined with respect to the direction in which the inspection light impinges, and the light reflected by the front surface or the rear surface of the protective window member, which is a factor that hinders the improvement of sensitivity, is consequently reflected at an angle with respect to the incident light. Consequently, the orientation of the light reflected by the protective window member deviates from the orientation of the light reflected by the inspection object surface and, attendant therewith, emerges from the optical path modifying means, thus creating a deviation between the direction of the light reflected by the inspection object surface and the direction of the light reflected by the protective window member. Thereby, the light reflected by the inspection object surface can be separated from the light reflected by the protective window member and guided to the inspection apparatus, which makes it possible to perform high precision detection.

In the third aspect of the invention, the protective window member may be installed at a tip region of the head tube; and the normal line direction of at least one of the front surface and the rear surface of the protective window member may be inclined toward a tip side of the head tube as it goes toward the outer side of the head tube in the radial direction. According to this aspect, the inspection light is bends toward the tip side of the head tube by at least one of the front surface and the rear surface of the protective window member, and consequently the position at which the inspection light impinges the inspection object is biased to the tip side of the head tube compared with the case wherein the protective window member is not provided. Accordingly, if the inspection object is blind hole shaped and the head tube is inserted in the inspection object, then, for example, the head tube will collide with the tip of the inspection object, and a dead angle will arise because the inspection light will no longer reach the tip; however, according to the present aspect, it is possible to perform inspection further on the tip side.

In a third aspect of the invention, the normal line directions of the front surface and the rear surface of the protective window member may be inclined at equal angles with respect to the direction in which the inspection light impinges the protective window member. In this case, the front surface and the rear surface of the protective window member are parallel, and it is therefore possible to use a flat plate, which is easy to form and reduces cost.

BRIEF DESCRIPTION OF THE DRAWINGS

In the attached drawings:

FIG. 10 shows a protective window member and the optical path of the inspection light and the like;

DETAILED DESCRIPTION OF THE PREFERRED EMBODIMENTS

Figure 1:
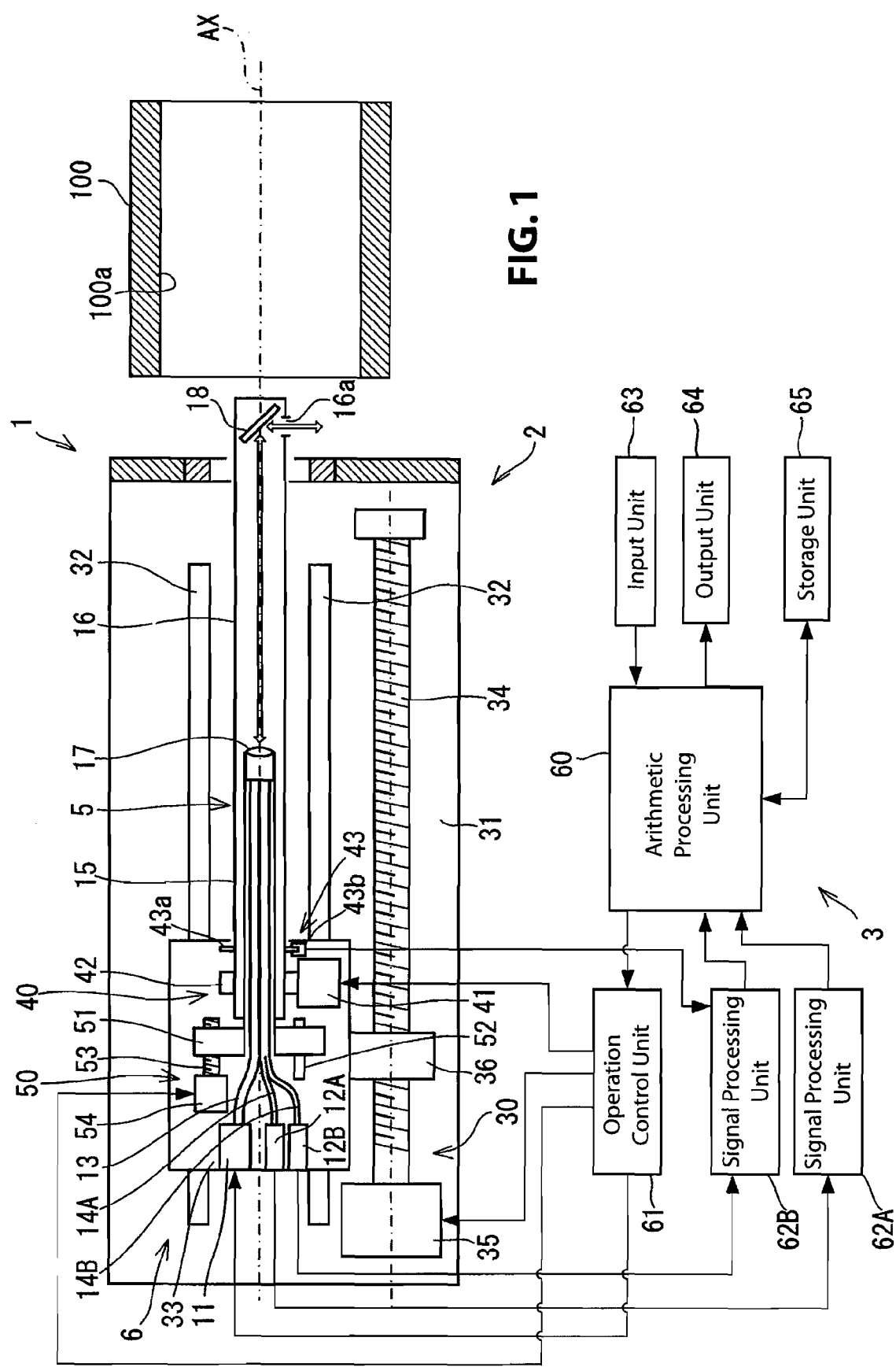
FIG. 1 is a schematic drawing that shows the configuration of one embodiment of a surface inspection apparatus of the present invention.

FIG. 1 shows a schematic diagram of the configuration of a surface inspection apparatus according to one embodiment of the present invention. A surface inspection apparatus 1 is an apparatus that is adapted to the inspection of an inner circumferential surface 100a of a cylindrical body of an inspection object 100. The surface inspection apparatus 1 comprises an inspection mechanism 2, which performs such inspection and outputs information related to the inner circumferential surface 100a of the inspection object 100, and a control unit 3 that controls the operation of each part of the inspection mechanism 2 and manages the information output by the inspection mechanism 2. Furthermore, the inspection mechanism 2 comprises: a detection unit 5 that projects inspection light to the inspection object 100 and receives light reflected by the inspection object 100; and a drive unit 6 that causes the detection unit 5 to perform a prescribed operation.

The detection unit 5 comprises: a laser diode (hereinbelow, called LD) 11, which serves as the light source of the inspection light; two photodetectors (hereinbelow, called PDs) 12A, 12B, each of which receives light reflected by the inspection object 100 and outputs an electrical signal wherein the current or voltage varies with the amount of light per unit of time (reflected light intensity) of that reflected light; a light projecting fiber 13 that guides the inspection light that emerges from the LD 11 toward the inspection object 100; a first light receiving fiber group 14A that guides the light reflected by the inspection object 100 to the PD 12A; a second light receiving fiber group 14B that guides the light reflected by the inspection object 100 to the PD 12B; a holding tube 15 that holds the light projecting fiber 13 and the light receiving fiber groups 14A, 14B in a bundled state; and a hollow shaft shaped inspection head 16, which is provided so that it is coaxial with the outer side of the holding tube 15.

Figure 2:
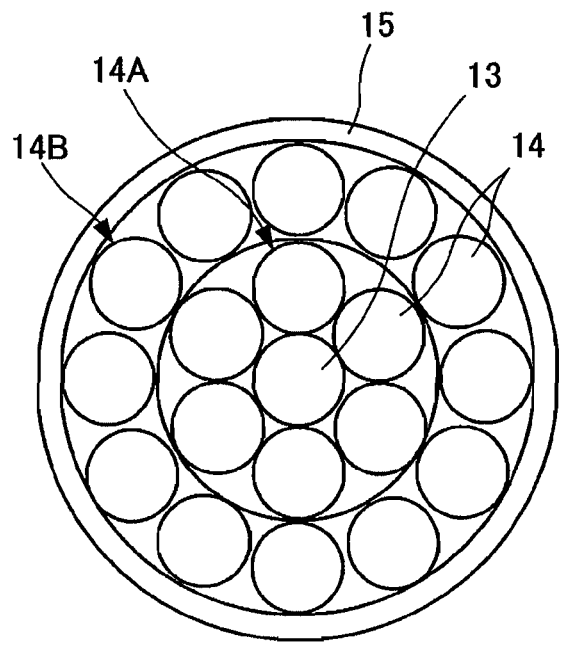
FIG. 2 is a plan view schematic diagram that shows a tip part of a light projecting fiber and a light receiving fiber group, which are held by a holding tube.

FIG. 2 shows a tip parts (right end parts in FIG. 1) of the light projecting fiber 13 and the light receiving fiber groups 14A, 14B, which are held by the holding tube 15. The light projecting fiber 13 is disposed along the center line of the holding tube 15, and the first light receiving fiber group 14A comprises six light receiving fibers 14, which are disposed around the light projecting fiber 13. In addition, the second light receiving fiber group 14B comprises twelve light receiving fibers 14, which are disposed on the outer side of the first light receiving fiber group 14A from the perspective of the light projecting fiber 13. The light projecting fiber 13 and the light receiving fibers 14 that constitute the light receiving fiber groups 14A, 14B are fixed to one another by a joining means such as a resin adhesive (not shown), which prevents positional deviation. Furthermore, the number of light receiving fibers 14 that constitute the first light receiving fiber group 14A and the second light receiving fiber group 14B is not limited, and any appropriate number may be used.

As shown in FIG. 1, a lens 17 is provided to the tip of the holding tube 15 that causes the inspection light, which was guided through the light projecting fiber 13, to emerge in a beam shape along the directions of an axis AX (hereinbelow, called the axial directions) of the inspection head 16, and condenses the reflected light, which travels in a direction that is the reverse of that of the inspection light along the axial directions of the inspection head 16, and directs it to the light receiving fibers 14. A mirror 18, which serves as an optical path modifying means, is fixed to the tip part (the right end part in FIG. 1) of the inspection head 16, and a translucent window 16a is provided to the outer circumference of the inspection head 16 so that it opposes the mirror 18. The mirror 18 modifies the optical path of the inspection light that emerges from the lens 17 so that it leads toward the translucent window 16a, and also modifies the optical path of the reflected light that enters the inspection head 16 from the translucent window 16a so that the path follows a direction that proceeds toward the lens 17.

The drive unit 6 comprises a linear drive mechanism 30, a rotary drive mechanism 40, and a focal point adjusting mechanism 50. The linear drive mechanism 30 is provided as a moving means that moves the inspection head 16 in its axial directions. To implement this function, the linear drive mechanism 30 comprises a base 31, a pair of rails 32 that are fixed to the base 31, a slider 33 that can move along the rails 32 in the axial directions of the inspection head 16, a feed screw 34 that is disposed to the side of the slider 33 and parallel to the axis AX of the inspection head 16, and an electric motor 35 that rotationally drives the feed screw 34. The slider 33 functions as a means for supporting the entirety of the detection unit 5. Namely, the LD 11 and the PDs 12A, 12B are fixed to the slider 33, the inspection head 16 is attached to the slider 33 via the rotary drive mechanism 40, and the holding tube 15 is attached to the slider 33 via the focal point adjusting mechanism 50. Furthermore, the feed screw 34 is screwed to a nut 36, which is fixed to the slider 33. Accordingly, the electric motor 35 rotationally drives the feed screw 34, which moves the slider 33 along the rails 32 in the axial directions of the inspection head 16, and, attendant therewith, the entirety of the detection unit 5, which is supported by the slider 33, moves in the axial directions of the inspection head 16. Using the linear drive mechanism 30 to drive the detection unit 5 makes it possible to change the irradiation position of the inspection light on the inner circumferential surface 100a of the inspection object 100 relative to the axial directions of the inspection head 16.

The rotary drive mechanism 40 is provided as a rotary driving means that rotates the inspection head 16 around the axis AX. To implement such a function, the rotary drive mechanism 40 comprises a bearing (not shown) that supports the inspection head 16 so that it is freely rotatable around the axis AX, an electric motor 41 that serves as a rotary drive source, and a transmission mechanism 42 that transmits the rotation of the electric motor 41 to the inspection head 16. A well known rotation transmitting mechanism, such as a belt transmission apparatus or a gear train, may be used as the transmission mechanism 42. Transmitting the rotation of the electric motor 41 to the inspection head 16 via the transmission mechanism 42 rotates the inspection head 16, along with the mirror 18 fixed therein, around the axis AX. Using the rotary drive mechanism 40 to rotate the inspection head 16 makes it possible to change the irradiation position of the inspection light on the inner circumferential surface 100a of the inspection object 100 relative to the circumferential direction. Furthermore, combining the movement of the inspection head 16 in the axial directions with its rotation around the axis AX makes it possible to scan the inspection light over the entire surface of the inner circumferential surface 100a of the inspection object 100. Furthermore, the holding tube 15 does not rotate when the inspection head 16 rotates. Furthermore, a rotary encoder 43 is provided to the rotary drive mechanism 40 that outputs a pulse signal in accordance with the rotational position of the inspection head 16. The rotary encoder 43 comprises: a disc 43a, which is attached to and rotates integrally with the inspection head 16, wherein a plurality of detection holes (not shown) are formed lined up along the circumferential direction at prescribed intervals; and a pulse generation unit 43b that generates pulses in accordance with the positions of the detection holes of the disc 43a. The control unit 3 uses the pulse signal from the rotary encoder 43.

The focal point adjusting mechanism 50 is provided as a focal point adjusting means that drives the holding tube 15 in the directions of the axis AX so that the inspection light focuses on the inner circumferential surface 100a of the inspection object 100, and so that the light reflected by the inner circumferential surface 100a focuses on either the first light receiving fiber group 14A or the second light receiving fiber group 14B. To implement this function, the focal point adjusting mechanism 50 comprises: a support plate 51, which is fixed to a base end part of the holding tube 15; a rail 52, which is disposed between the support plate 51 and the slider 33 of the linear drive mechanism 30, that guides the support plate 51 in the axial directions of the inspection head 16; a feed screw 53, which is disposed parallel to the axis AX of the inspection head 16, that screws into the support plate 51; and an electric motor 54 that rotationally drives the feed screw 53. Rotationally driving the feed screw 53 by using the electric motor 54 moves the support plate 51 along the rail 52 and moves the holding tube 15 in the axial directions of the inspection head 16. Thereby, it is possible to adjust the length of the optical path from the lens 17 through the mirror 18 to the inner circumferential surface 100a so that the inspection light focuses on the inner circumferential surface 100a of the inspection object 100 and so that the light reflected by the inner circumferential surface 100a focuses on either the first light receiving fiber group 14A or the second light receiving fiber group 14B.

The following explains the control unit 3. The control unit 3 comprises: an arithmetic processing unit 60, which functions as a computer unit that manages the inspection process performed by the surface inspection apparatus 1 and executes, for example, a measurement result process; an operation control unit 61 that, in accordance with instructions from the arithmetic processing unit 60, controls the operation of each part of the inspection mechanism 2; a signal processing unit 62A that performs a prescribed process on the output signal of the PD 12A; a signal processing unit 62B that performs a prescribed process on the output signal of the PD 12B; an input unit 63 that a user can use to input instructions to the arithmetic processing unit 60; an output unit 64 that presents, for example, measurement results in the arithmetic processing unit 60 to the user; and a storage unit 65 that stores, for example, measurement data and a computer program to be executed by the arithmetic processing unit 60. The arithmetic processing unit 60, the input unit 63, the output unit 64, and the storage unit 65 can be configured by using general purpose computer equipment such as a personal computer. In this case, the input unit 63 is provided with input equipment, such as a keyboard and a mouse, and the output unit 64 is provided with a monitor device. The output unit 64 may be supplemented with output equipment such as a printer. A hard disk storage apparatus and a memory device, such as a semiconductor memory device that has a memory retention capability, are used as the storage unit 65. The operation control unit 61 and the signal processing units 62A, 62B may be implemented by a hardware control circuit, or they may be implemented by a computer unit.

The following illustrates a preferred embodiment for a case wherein the inspection object 100 is assumed to be a casting for which the inner circumferential surface 100a has undergone a cutting process. As the inspection modes that can be executed by the surface inspection apparatus 1, it is possible to set: a surface defect inspection mode that detects defects of the surface itself, such as a blow hole that appears in the inner circumferential surface 100*a*, which serves as the surface of the inspection object 100; and an surface foreign matter inspection mode, which detects foreign matter, such as chips that adhere to the surface of the inspection object 100, as defects; in addition, each inspection mode can be selected in accordance with an instruction given by the user via the input unit 63. Furthermore, the operation of the arithmetic processing unit 60 and the operation control unit 61 do differ by inspection mode; however, operation that is common to all modes will be explained first.

When inspecting the surface of the inner circumferential surface 100*a* of the inspection object 100, the inspection object 100 is disposed so that it is coaxial with the inspection head 16. At the start of the inspection, the arithmetic processing unit 60 issues an instruction to the operation control unit 61, in accordance with an instruction from the input unit 63, to start the operation needed to inspect the inner circumferential surface 100*a* of the inspection object 100. The operation control unit 61, which receives that instruction, causes the LD 11 to emit light with a prescribed intensity and controls the operation of the motor 35 and the motor 41 so that the inspection head 16 moves in its axial directions and rotates around the axis AX at a constant speed. Furthermore, if the surface defect inspection mode is selected by the user's instruction, then the operation control unit 61 controls the operation of the motor 54 so that the inspection light focuses on the inner circumferential surface 100*a* and so that the light reflected by the inner circumferential surface 100*a* focuses on the second light receiving fiber group 14B. Moreover, if the surface foreign matter inspection mode is selected, then the operation control unit 61 controls the operation of the motor 54 so that the inspection light focuses on the inner circumferential surface 100*a* and so that the light reflected by the inner circumferential surface 100*a* focuses on the first light receiving fiber group 14A. By controlling the operation in this manner, the inner circumferential surface 100*a* is scanned by the inspection light from one end to the other.

Linked with that scanning, the output signal of the PD 12A and the output signal of the PD 12B are successively conducted to the signal processing unit 62A and the signal processing unit 62B, respectively. The signal processing unit 62A performs analog signal processing on the output signal of the PD 12A, which is needed for the arithmetic processing unit 60 to process that signal, subsequently performs A/D conversion of that processed analog signal with a prescribed bit depth, and outputs the obtained digital signal to the arithmetic processing unit 60 as a reflected light signal. The A/D conversion performed by the signal processing unit 62A uses a pulse train, which is output from the rotary encoder 43, as a sample clock signal. Thereby, a gradational digital signal is generated that is correlated with the amount of light received (intensity) by the PDs 12 while the inspection head 16 is undergoing a prescribed angular rotation, and that signal is output from the signal processing unit 62A. The signal processing unit 62B, which inputs the output signal of the PD 12B, functions in a manner that is similar to that described above.

The arithmetic processing unit 60, which receives the reflected light signals from the signal processing units 62A, 62B, stores the signal from the signal processing unit 62A and the signal from the signal processing unit 62B in the storage unit 65 in a state wherein they can be distinguished from one another. Furthermore, the arithmetic processing unit 60 uses the reflected light signals stored in the storage unit 65 to generate a two dimensional image, which is a planar unfolding of the inner circumferential surface 100*a* of the inspection object 100, determines whether there is a defect based on that two dimensional image, and outputs the inspection result as the determination result to the output unit 64.

Figure 3:
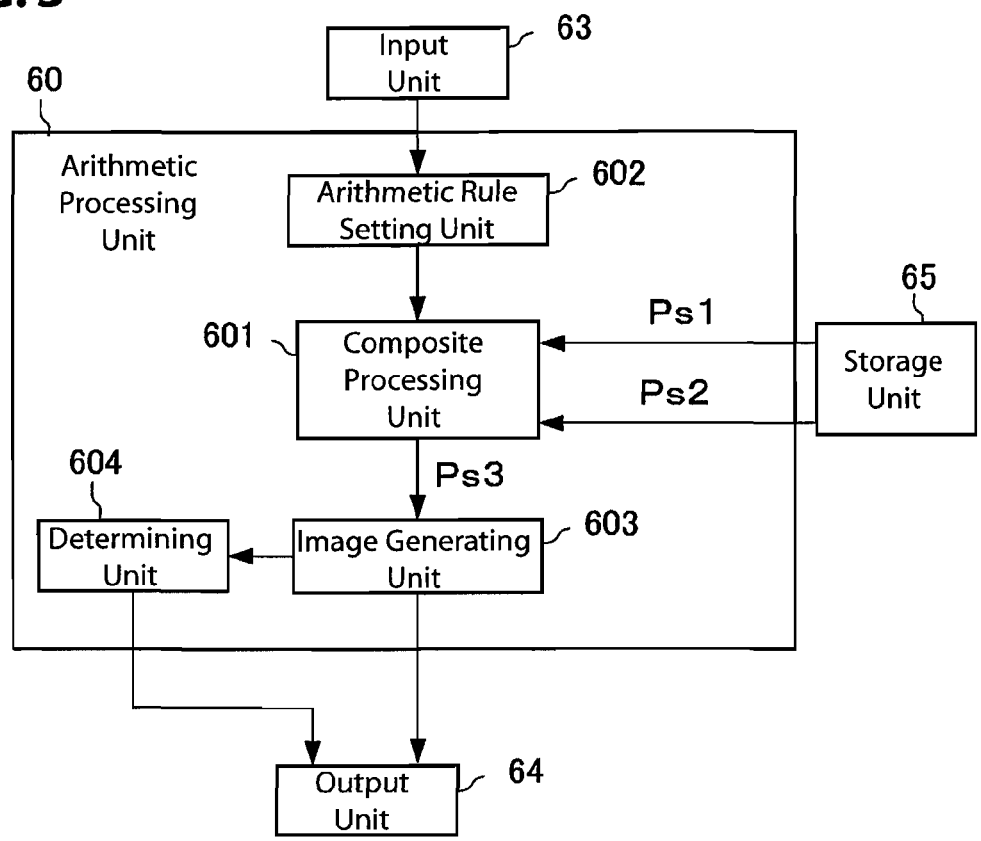
FIG. 3 is a block diagram that explains the functions of an arithmetic processing unit.

Using FIG. 3 as a reference, the following explains a process wherein the arithmetic processing unit 60 generates such a two dimensional image and outputs an inspection result based thereon. FIG. 3 is a block diagram that explains the function of the arithmetic processing unit 60. By executing a prescribed program stored in the storage unit 65, the arithmetic processing unit 60 functions as a composite processing unit 601, an arithmetic rule setting unit 602, an image generating unit 603, and a determining unit 604, as shown in FIG. 3. First, the arithmetic processing unit 60 reads a reflected light signal Ps1, which is based on the output signal of the PD 12A stored in the storage unit 65, and a reflected light signal Ps2, which is based on the output signal of the PD 12B, into the composite processing unit 601. Next, the composite processing unit 601 combines these signals Ps1, Ps2 in accordance with an arithmetic rule, which is set by the arithmetic rule setting unit 602, and outputs that composite signal to the image generating unit 603. The arithmetic rule setting unit 602 holds an arithmetic rule that corresponds to the surface defect inspection mode and an arithmetic rule that corresponds to the surface foreign matter inspection mode, which were discussed above, and, based on the instruction from the input unit 63, sets an arithmetic rule that corresponds to the selected inspection mode.

The arithmetic rules held by the arithmetic rule setting unit 602 are set by taking into consideration the characteristic (sensitivity characteristic) of the output signal of each of the PDs 12A, 12B with respect to changes in the properties of the inner circumferential surface 100*a* of the inspection object 100, i.e., changes in the properties of the reflected light. The arithmetic rule that is set in the surface defect inspection mode will be explained first. In the surface defect inspection mode, the arithmetic rule is set so that a sensitivity characteristic is obtained wherein it is possible to distinguish a defect, such as a blow hole that appears in the inner circumferential surface 100*a* of the inspection object 100, from a hollow in the inner circumferential surface 100*a* formed by the cutting process, which should not be considered a defect. Furthermore, when a cutting process is performed, hollows are unavoidable and are shallow—very similar to so-called chatter marks that appear in a surface when a tool, such as a cutting tool, is replaced with a new one. Hollows formed in the inner circumferential surface 100*a* of the inspection object 100 change the direction of the reflected light. In other words, a hollow can be considered to be a surface that is angled to a certain degree with respect to the irradiation direction (optical axis) of the inspection light.

Figure 4:
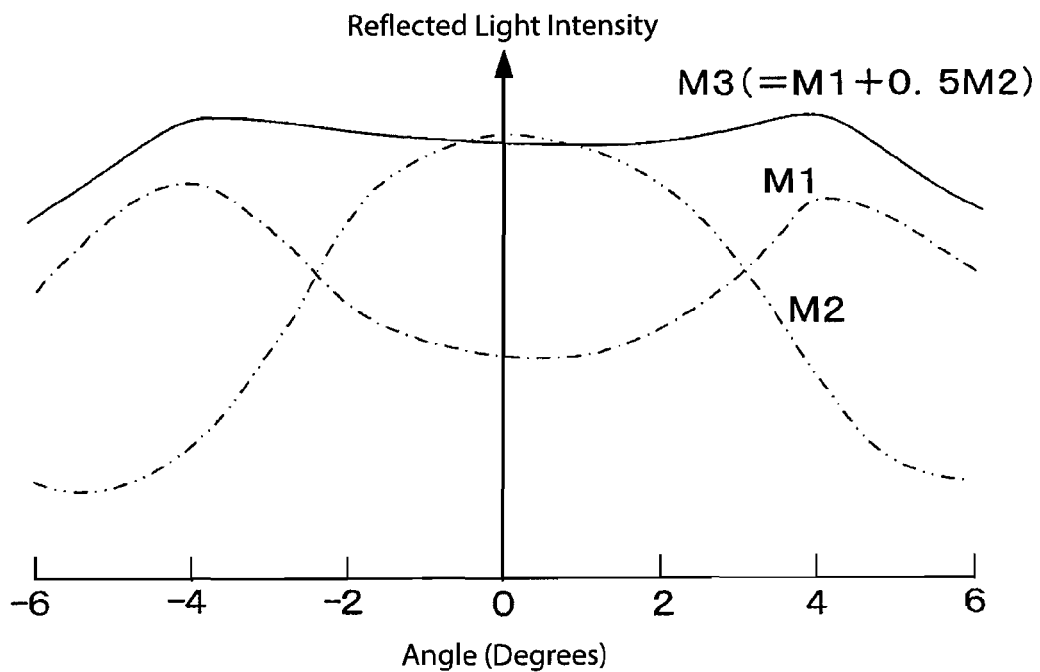
FIG. 4 shows the sensitivity characteristic of a detection unit with respect to angular changes in reflected light.

FIG. 4 shows the sensitivity characteristic of the detection unit 5 in relation to changes in the angle of the reflected light. In FIG. 4, a chain line M1 indicates the output signal of the PD 12A, i.e., the sensitivity characteristic of the first light receiving fiber group 14A, for the case wherein the angle of the reflected light changes; a chain double dashed line M2 indicates the output signal of the PD 12B, i.e., the sensitivity characteristic of the second light receiving fiber group 14B, for the case wherein the angle of the reflected light changes; and a solid line M3 indicates the sensitivity characteristic for the case wherein the output signal of the PD 12A and the output signal of the PD 12B are combined. The abscissa in FIG. 4 represents the angle (in degrees), and the ordinate represents the reflected light intensity. In the surface defect inspection mode, the detection unit 5 is adjusted so that the reflected light focuses on the second light receiving fiber group 14B, as discussed above. Consequently, as shown by the chain double dashed line M2, the sensitivity characteristic of the second light receiving fiber group 14B has its maximum value at the origin where there is no deviation in the direction of the reflected light, and the intensity decreases as the deviation of the reflected light increases. Moreover, as shown by the chain double dashed line M1 the sensitivity characteristic of the first light receiving fiber group 14A has maximum values in the vicinity of +4° and −4° and a depressed center, which is the minimum value, at the origin on account of the fact that the focus is on the second light receiving fiber group 14B. These sensitivity characteristics are dependent on physical configuration, such as the spacing between optical fiber groups 14A, 14B, the distance between the light projecting fiber 13 and each of the fiber groups 14A, 14B, and the size of the diameter of the light receiving fibers 14 that constitute these fiber groups, and therefore are particular to the embodiment of the detection unit 5.

The abovementioned hollow formed in the inner circumferential surface 100a changes the angle of the reflected light in a range of approximately −6° to +6°. Accordingly, if the detection unit 5 is provided with a sensitivity characteristic that is substantially flat with respect to angular change within this range, then the intensity of the reflected light received by the detection unit 5 does not decrease even if the hollow is irradiated with the inspection light, and it is therefore possible to clearly distinguish the hollow from a blow hole. Accordingly, in the surface defect inspection mode of the present embodiment, an arithmetic rule is set that multiplies the output signal of the PD 12A by 0.5 as a prescribed value and then adds that to the output signal of the PD 12B so that the sensitivity characteristic is substantially flat with respect to an angular change within a range of approximately −6° to +6°, as described by the solid line M3 in FIG. 4.

The following explains the arithmetic rule set in the surface foreign matter inspection mode. In the surface foreign matter inspection mode, the arithmetic rule is set so that a sensitivity characteristic is obtained that can sense foreign matter, even if the inspection light irradiated on foreign matter, such as chips that adhere to the inner circumferential surface 100a of the inspection object 100, reflects in a similar manner to a normal surface that does not have foreign matter. If foreign matter, such as chips, adheres to the inner circumferential surface 100a, then, compared to the case where there is no foreign matter, the reflection position of the inspection light becomes closer to the that extent foreign matter is present. In other words, if foreign matter adheres, then the length of the optical path from the lens 17 to the inner circumferential surface 100a via the mirror 18 is shorter than for the case where there is no foreign matter.

Figure 5:
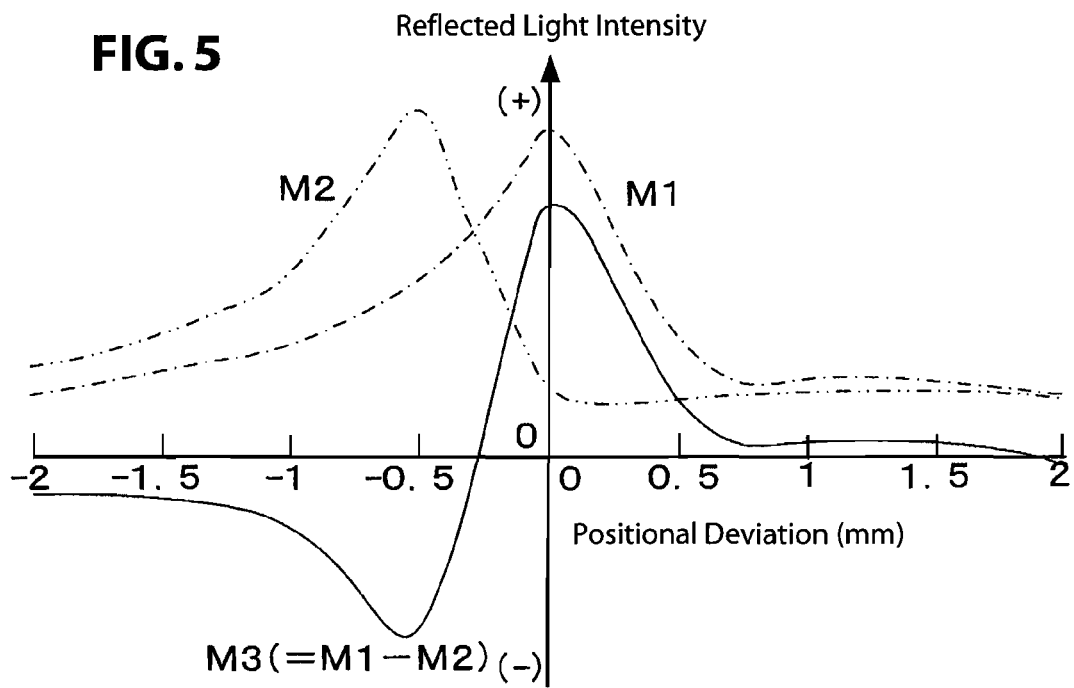
FIG. 5 shows the sensitivity characteristic of the detection unit with respect to changes in the distance from an inspection object to a reflection position.

FIG. 5 shows the sensitivity characteristic of the detection unit 5 in relation to changes in the distance to the reflection position on the inspection object 100. The chain line M1 in FIG. 5 represents the output signal of the PD 12A, i.e., the sensitivity characteristic of the first light receiving fiber group 14A, for the case wherein the distance to the reflection position changes; the chain double dashed line M2 represents the output signal of the PD 12B, i.e., the sensitivity characteristic of the second light receiving fiber group 14B, for the case wherein the distance to the reflection position changes; and the solid line M3 represents the sensitivity characteristic for the case wherein the output signal of the PD 12A and the output signal of the PD 12B are combined. The abscissa in FIG. 5 represents the positional deviation (in mm) between the reference position and the reflection position, with the reference position as the origin. The minus sign indicates closeness to the detection unit 5 side. The ordinate in FIG. 5 represents the reflected light intensity. In the surface foreign matter inspection mode, the detection unit 5 is adjusted so that the reflected light focuses on the first light receiving fiber group 14A, as discussed above. Consequently, as shown by the chain line M1, the sensitivity characteristic of the first light receiving fiber group 14A has its maximum value at the origin, where there is no positional deviation, and the intensity decreases as the positional deviation increases. Moreover, the sensitivity characteristic of the second light receiving fiber group 14B is equivalent to the sensitivity characteristic of the first light receiving fiber group 14A shifted to the vicinity of −0.5 mm on account of the fact that the focus is on the first light receiving fiber group 14A. These sensitivity characteristics are dependent on the physical configuration of the detection unit 5, as discussed above, and are particular to the embodiment of the detection unit 5.

Because the average dimension (e.g., thickness) of a chip that adheres to the inner circumferential surface 100a is approximately 0.5 mm, if a chip adhered to the inner circumferential surface 100a is irradiated with inspection light, then its reflection position becomes closer by approximately 0.5 mm compared with the reference position when there is no chip. Accordingly, if the detection unit 5 is provided with a sensitivity characteristic that has a negative peak at which it is possible to detect a condition in which the reflection position becomes closer by approximately that order, then it is possible to detect foreign matter even if the inspection light irradiated on foreign matter, such as a chip, reflects similarly to that of a normal surface that does not have foreign matter. Accordingly, in the surface foreign matter inspection mode of the present embodiment, an arithmetic rule is set that subtracts the output signal of the PD 12B from the output signal of the PD 12A so that the sensitivity characteristic has a negative peak at approximately −0.5 mm, as shown by the solid line M3 in FIG. 5.

Each of the arithmetic rules explained above are merely examples of rules adapted to the physical configuration of the detection unit 5—specifically, the spacing between the optical fiber groups 14A, 14B, the distance between the light projecting fiber 13 and each of the fiber groups 14A, 14B, and the size of the diameter of the light receiving fibers 14 that constitute these fiber groups—and other arithmetic rules can be used to obtain prescribed sensitivity characteristics.

As shown in FIG. 3, the image generating unit 603 receives a composite signal Ps3, wherein the signals are combined in accordance with the arithmetic rule that corresponds to each inspection mode, from the composite processing unit 601, uses that composite signal Ps3 to generate a two dimensional image, wherein the inner circumferential surface 100a of the inspection object 100 is planarly unfolded, and outputs that two dimensional image to the output unit 64 and the determining unit 604. The two dimensional image generated by the image generating unit 603 corresponds to an image wherein the inner circumferential surface 100a is unfolded in a plane defined by an orthogonal biaxial coordinate system, e.g., with the circumferential direction of the inspection object as the x axial directions and the axial directions of the inspection head 16 as the y axial directions. By processing the two dimensional image obtained from the image generating unit 603 with a prescribed algorithm, which is prepared for each inspection mode, the determining unit 604 determines the presence of any defect that exceeds a permissible limit and outputs that determination result to the output unit 64.

As explained above, according to the surface inspection apparatus 1 of the present embodiment, the reflected light signal Ps1, which is based on the output signal of the PD 12A, and the reflected light signal Ps2, which is based on the output signal of the PD 12B, are combined in accordance with an arithmetic rule that corresponds to each inspection mode, and it is thereby possible to generate the sensitivity characteristic of the detection unit 5 that is appropriate for each inspection mode. Thereby, it is possible with a single detection unit 5 to execute a plurality of different inspections, and the inspection accuracy in each inspection mode is improved.

In the above embodiment, the LD 11 corresponds to a light source according to the present invention, the PD 12A corresponds to a first photoelectric converting means according to the present invention, the PD 12B corresponds to a second photoelectric converting means according to the present invention, the first light receiving fiber group 14A corresponds to a first light receiving fiber group according to the present invention, and the second light receiving fiber group 14B corresponds to a second light receiving fiber group according to the present invention.

However, the present invention is not limited to the above embodiment and may be implemented by a variety of embodiments. In the embodiment described above, the output signals from the PDs 12A, 12B are A/D converted, and then the arithmetic processing unit 60 is caused to function so that these digital signals are combined in accordance with a prescribed arithmetic rule; however, the composite processing unit 601 and the arithmetic rule setting unit 602 shown in FIG. 3 may each be implemented by a hardware circuit so that the output signals from the PDs are combined in accordance with a prescribed arithmetic rule in their state as analog signals.

In the embodiment discussed above, two light receiving fiber groups 14A, 14B are provided that have different positional relationships with respect to the light projecting fiber 13, as shown in FIG. 2; however, three light receiving fiber groups may be provided by disposing a plurality of light receiving fibers at the outer circumference of the second light receiving fiber group 14B. If three light receiving fiber groups are provided, then a third photoelectric converting means may be provided that receives the reflected light guided from the outermost third light receiving fiber group. This increases the number of ways that the signals of the photoelectric converting means can be combined, which makes it possible to provide a variety of sensitivity characteristics to the detecting means.

A variety of arithmetic rules, which are set by the arithmetic rule setting unit 602, are conceivable. For example, in the surface foreign matter inspection mode discussed above, the signal of the PD 12B is subtracted from the signal of the PD 12A; however, the signal of the PD 12A may be subtracted from the signal of the PD 12B after focusing the reflected light on the second light receiving fiber group 12B. In so doing, it is possible to obtain a sensitivity characteristic that inverts the solid line M3 shown in FIG. 5 with respect to the ordinate. In this case, it is possible to detect the state wherein the reflection position is spaced apart by a prescribed distance from the reference position. Thereby, it is possible to detect a recessed part, which is formed in the surface of the inspection object, that has a dimension that corresponds to the prescribed distance.

In addition, setting an arithmetic rule that simply adds the signal of the PD 12A and the signal of the PD 12B makes it possible to obtain a sensitivity characteristic that is substantially equivalent to the case wherein a single light receiving fiber group is provided that has a light receiving surface area that is the sum of the light receiving surface areas of those fiber groups, i.e., a case wherein the diameter of each of the light receiving fibers is enlarged. Furthermore, it is not essential to use both of these signals; as needed, these signals can be used singularly.

The inspection apparatus 1 discussed above was adapted to the inspection of a cylindrically shaped inner circumferential surface, but it can also be adapted to an inspection apparatus that inspects an inspection object that has a planar surface by moving the inspection head 16 in its axial directions—without rotating it—while moving it in directions that are orthogonal to its axial directions. The surface foreign matter inspection mode discussed above has the sensitivity characteristic shown in FIG. 5 related to changes in the reflection position, and it is therefore possible to make the surface inspection apparatus 1 function as a rotary type distance measuring apparatus that can derive the circularity of the inspection object with a prescribed resolution.

Figure 6:
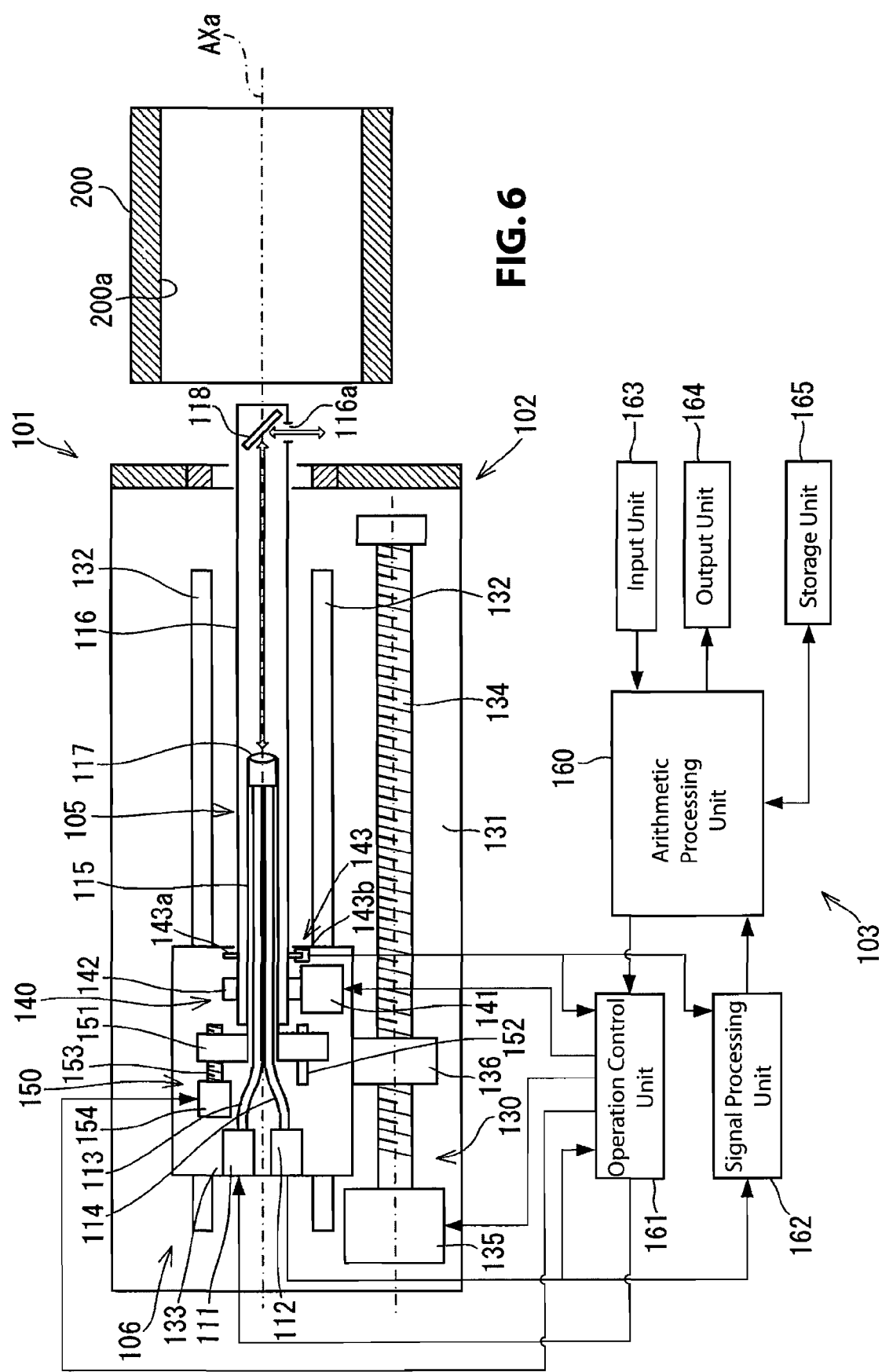
FIG. 6 is a schematic drawing of the configuration of another embodiment of the surface inspection apparatus of the present invention.

FIG. 6 is a schematic drawing of the configuration of another embodiment of the surface inspection apparatus of the present invention. A surface inspection apparatus 101 is an apparatus that is adapted to the surface inspection of an inner circumferential surface 200a of a cylindrical body 200, which is the inspection object, such as the cylinder liner or the cylinder bore of an internal combustion engine. The surface inspection apparatus 101 comprises: an inspection mechanism 102, which performs such inspection and outputs information related to the inner circumferential surface 200a of the cylindrical body 200; and control unit 103 that controls the operation of each part of the inspection mechanism 102 and processes the information output thereby. Furthermore, the inspection mechanism 102 comprises: a detection unit 105 that projects inspection light to the inspection object 200 and receives the light reflected thereby; and a drive unit 106 that causes the detection unit 105 to perform a prescribed operation.

The detection unit 105 comprises: a laser diode (hereinbelow, called LD) 111, which serves as the light source of the inspection light; a photodetector (hereinbelow, called PD) 112 that receives light reflected by the inspection object 200 and outputs a current or voltage electrical signal in accordance with the amount of light (reflected light intensity) per unit of time of that reflected light; a light projecting fiber 113 that guides the inspection light emitted from the LD 111 toward the inspection object 200; light receiving fibers 114 that guide the light reflected by the inspection object 200 to the PD 112; a holding tube 115 that holds the fibers 113, 114 in a bundled state; and a hollow, shaft shaped inspection head 116, which is provided so that it is coaxial with the outer side of the holding tube 115. A lens 117 is provided to the tip of the holding tube 115 that causes the inspection light, which was guided through the light projecting fiber 113, to emerge in a beam shape along the directions of an axis AXa (hereinbelow, called the axial directions) of the inspection head 116, and condenses the reflected light, which travels in a direction that is the reverse of that of the inspection light along the axial directions of the inspection head 116, and directs it to the light receiving fibers 114. A mirror 118, which serves as an optical path modifying means, is fixed to the tip part (the right end part in FIG. 6) of the inspection head 116, and a translucent window 116a is provided to the outer circumference of the inspection head 116 so that it opposes the mirror 118. The mirror 118 modifies the optical path of the inspection light that emerges from the lens 117 so that it leads toward the translucent window 116a, and also modifies the optical path of the reflected light that enters the inspection head 116 from the translucent window 116a so that the path follows a direction that proceeds toward the lens 117.

The drive unit 106 comprises a linear drive mechanism 130, a rotary drive mechanism 140, and a focal point adjusting mechanism 150. The linear drive mechanism 130 is provided as a moving means that moves the inspection head 116 in its axial directions. To implement this function, the linear drive mechanism 130 comprises a base 131, a pair of rails 132 that are fixed to the base 131, a slider 133 that can move along the rails 132 in the axial directions of the inspection head 116, a feed screw 134 that is disposed to the side of the slider 133 and parallel to the axis AXa of the inspection head 116, and an electric motor 135 that rotationally drives the feed screw 134. The slider 133 functions as a means for supporting the entirety of the detection unit 105. Namely, the LD 111 and the PD 112 are fixed to the slider 133, the inspection head 116 is attached to the slider 133 via the rotary drive mechanism 140, and the holding tube 115 is attached to the slider 133 via the focal point adjusting mechanism 150. Furthermore, the feed screw 134 is screwed to a nut 136, which is fixed to the slider 133. Accordingly, the electric motor 135 rotationally drives the feed screw 134, which moves the slider 133 along the rails 132 in the axial directions of the inspection head 116, and, attendant therewith, the entirety of the detection unit 105, which is supported by the slider 133, moves in the axial directions of the inspection head 116. Using the linear drive mechanism 130 to drive the detection unit 105 makes it possible to change the irradiation position of the inspection light on the inner circumferential surface 200a of the inspection object 200 relative to the axial directions of the inspection head 116.

The rotary drive mechanism 140 is provided as a rotary driving means that rotates the inspection head 116 around the axis AXa. To implement such a function, the rotary drive mechanism 140 comprises a bearing (not shown) that supports the inspection head 116 so that it is freely rotatable around the axis AXa, an electric motor 141 that serves as a rotary drive source, and a transmission mechanism 142 that transmits the rotation of the electric motor 141 to the inspection head 116. A well known rotation transmitting mechanism, such as a belt transmission apparatus or a gear train, may be used as the transmission mechanism 142. Transmitting the rotation of the electric motor 141 to the inspection head 116 via the transmission mechanism 142 rotates the inspection head 116, along with the mirror 118 fixed therein, around the axis AXa. Using the rotary drive mechanism 140 to rotate the inspection head 116 makes it possible to change the irradiation position of the inspection light on the inner circumferential surface 200a of the inspection object 200 relative to the circumferential direction. Furthermore, combining the movement of the inspection head 116 in the axial directions with its rotation around the axis AXa makes it possible to scan the inspection light over the entire surface of the inner circumferential surface 200a of the inspection object 200. Furthermore, the holding tube 115 does not rotate when the inspection head 116 rotates. Furthermore, a rotary encoder 143 is provided to the rotary drive mechanism 140 that outputs a pulse signal in accordance with the rotational position of the inspection head 116. The rotary encoder 143 comprises: a disc 143a, which is attached to and rotates integrally with the inspection head 116, wherein a plurality of detection holes (not shown) are formed lined up along the circumferential direction at prescribed intervals; and a pulse generation unit 143b that generates pulses in accordance with the positions of the detection holes of the disc 143a. The control unit 103 uses the pulse signal from the rotary encoder 143.

The focal point adjusting mechanism 150 is provided as a focal point adjusting means that drives the holding tube 115 in the directions of the axis AXa so that the inspection light focuses on the inner circumferential surface 200a of the inspection object 200. To implement this function, the focal point adjusting mechanism 150 comprises: a support plate 151, which is fixed to a base end part of the holding tube 115; a rail 152, which is disposed between the support plate 151 and the slider 133 of the linear drive mechanism 130, that guides the support plate 151 in the axial directions of the inspection head 116; a feed screw 153, which is disposed parallel to the axis AXa of the inspection head 116, that screws into the support plate 151; and an electric motor 154 that rotationally drives the feed screw 153. Rotationally driving the feed screw 153 by using the electric motor 154 moves the support plate 151 along the rail 152 and moves the holding tube 115 in the axial directions of the inspection head 116. Thereby, it is possible to adjust the length of the optical path from the lens 117 through the mirror 118 to the inner circumferential surface 200a so that the inspection light focuses on the inner circumferential surface 200a of the inspection object 200.

The control unit 103 comprises: an arithmetic processing unit 160, which functions as a computer unit that manages the inspection process performed by the surface inspection apparatus 101 and executes, for example, a measurement result process; an operation control unit 161 that, in accordance with instructions from the arithmetic processing unit 160, controls the operation of each part of the inspection mechanism 102; a signal processing unit 162 that performs a prescribed process on the output signal of the PD 112; an input unit 163 that a user can use to input instructions to the arithmetic processing unit 160; an output unit 164 that presents, for example, measurement results in the arithmetic processing unit 160 to the user; and a storage unit 165 that stores, for example, measurement data and a computer program to be executed by the arithmetic processing unit 160. The arithmetic processing unit 160, the input unit 163, the output unit 164, and the storage unit 165 can be configured by using general purpose computer equipment such as a personal computer. In this case, the input unit 163 is provided with input equipment such as a keyboard and a mouse, and the output unit 164 is provided with a monitor device. The output unit 164 may be supplemented with output equipment such as a printer. A hard disk storage apparatus and a memory device, such as a semiconductor memory device that has a memory retention capability, are used as the storage unit 165.

Based on a variety of control signals from the arithmetic processing unit 160, the operation control unit 161 controls the operation of the LD 111 of the detection unit 105, the electric motor 135 of the linear drive mechanism 130, the electric motor 141 of the rotational drive mechanism 140, and the electric motor 154 of the focal point adjusting mechanism 150. Furthermore, the control of the electric motor 135 of the linear drive mechanism 130, the electric motor 141 of the rotational drive mechanism 140, and the electric motor 154 of the focal point adjusting mechanism 150 is not an essence of the present invention, and therefore a detailed explanation thereof is omitted.

Figure 7:
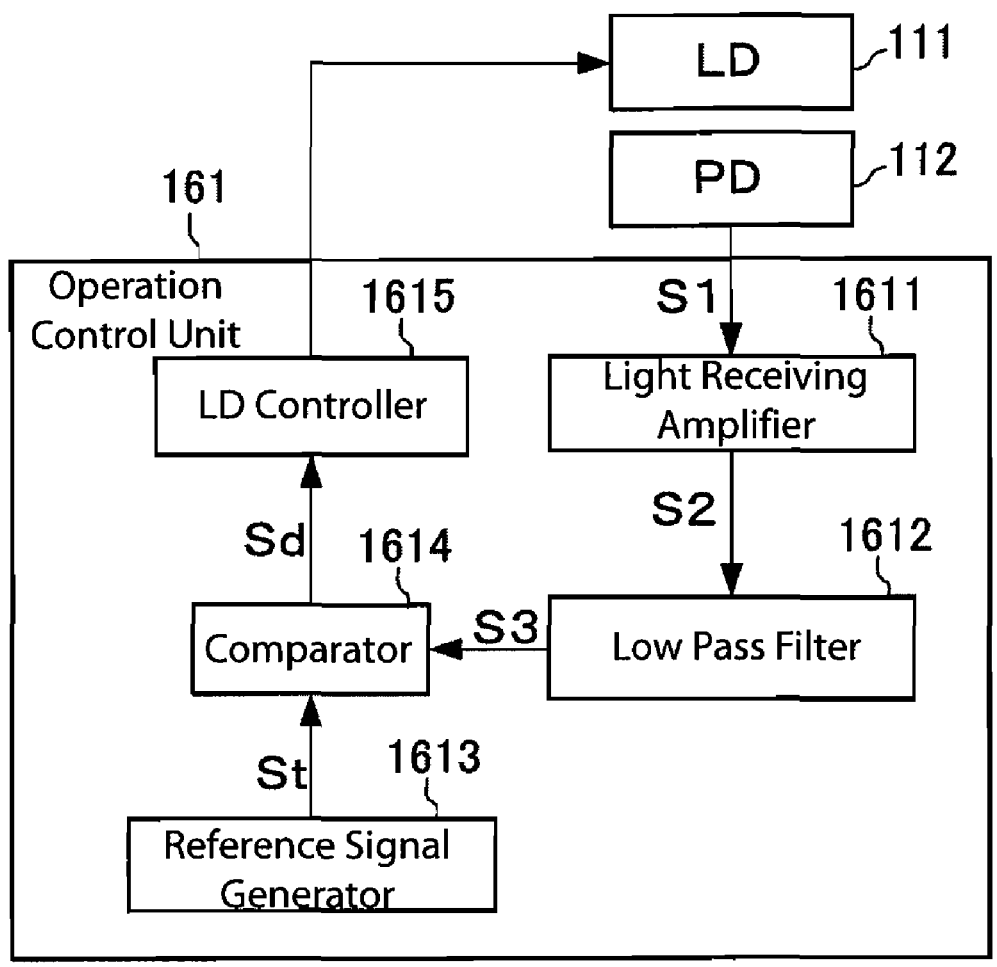
FIG. 7 is an explanatory diagram that explains the operation of the operation control unit in FIG. 6.

FIG. 7 is an explanatory diagram that explains the details of the operation control unit 161. The operation control unit 161 comprises: a light receiving amplifier 1611, which amplifies an output signal S1 that is output from the PD 112 and that corresponds to the light intensity; a low pass filter 1612 that cuts frequency components that exceed the upper limit of a prescribed range so that frequency components within that prescribed range are extracted from a signal S2 amplified by the amplifier 1611; a reference signal generator 1613 that outputs a preset reference signal St using a case wherein there is no defect on the inner circumferential surface 200a of the cylindrical body 200 as a reference; a comparator 1614 that compares a signal S3 that passes through the low pass filter 1612 and the reference signal St generated by the reference signal generator 1613, and outputs a differential signal Sd in accordance with that differential; and an LD controller 1615 that controls the LD 111 so that it is driven by a drive current in accordance with the differential signal Sd output by the comparator 1614.

The frequency components within the prescribed range extracted by their passage through the low pass filter 1612 contain frequency components that correspond to the fluctuations in the intensity of the reflected light caused by the deviation between the axis AXa and the center line of the cylindrical body 200. If the axis AXa and the center line of the cylindrical body 200 deviate, then, with every rotation of the inspection head 116, there are two occasions when the inspection head 116 and the inner circumferential surface 200a of the cylindrical body 200 are opposed, and the angle of incidence of the inspection light changes gradually while they are not opposed. Consequently, fluctuations that are attributable to this deviation have a frequency that is twice the rotational frequency of the inspection head 116. Accordingly, in the present embodiment, the prescribed range is set to a frequency range that is from two times to less than ten times the rotational frequency of the inspection head 116.

The LD controller 1615 is configured so that when there is a large differential between the reference signal St and the signal S3, which has frequency components in the prescribed range, the LD 111 is driven by a drive current that is large compared with the case wherein the differential is small, and so that, conversely, when the differential is small, the LD 111 is driven by a drive current that is small compared with the case wherein the differential is large. Thereby, when the differential is large, the LD 111 is controlled by the LD controller 1615 so that the intensity of the inspection light is high compared with the case wherein the differential is small. Consequently, fluctuations in the reflected light intensity, which has frequency components within the prescribed range, are offset by the LD controller 1615. The frequency of the intensity signal that corresponds to a defect is greater than approximately 1,000 times the rotational frequency of the inspection head 116, and is therefore not included in that prescribed range. Accordingly, there is no problem wherein a change in the intensity of the reflected light that corresponds to that defect is eliminated by the LD controller 1615.

In order to sample the signal output from the PD 112 a prescribed number of times with every rotation of the inspection head 116, the signal processing unit 162 frequency multiplies or divides the pulse signal from the rotary encoder 143 and uses such as the sampling clock. The signal sampled by the signal processing unit 162 is sent to the arithmetic processing unit 160. Based on that signal, the arithmetic processing unit 160 generates a two dimensional image related to the inner circumferential surface 200a of the inspection object 200 and determines whether a defect, such as a blow hole, is present. This determination determines whether a dark part that corresponds to a defect is present in the two dimensional image, but the details of that process and the details of other specific processes executed by the arithmetic processing unit 160 have little relevance to the essence of the present invention, and the explanations thereof are therefore omitted.

The above surface inspection apparatus 101 can eliminate fluctuations in the intensity of the reflected light because it controls the intensity of the inspection light in accordance with frequency components that correspond to fluctuations in the intensity of the reflected light that are attributable to a deviation between the axis AXa of the inspection head 116 and the center line of the cylindrical body 200. Moreover, because the frequency components that are extracted by passing the signal through the low pass filter 1612 are set to a prescribed range that has a certain width, it is also possible to eliminate changes in the intensity of the reflected light caused by fluctuations that have frequency components within the prescribed range, e.g., surface roughness of the inner circumferential surface 200a that is not related to axial deviation. Thereby, a two dimensional image that is not uneven can be used as the basis for the defect determination, which improves defect inspection accuracy.

In the above embodiment, the LD 111 corresponds to the light source according to the present invention, the PD 112 corresponds to a photoelectric converting means according to the present invention, the low pass filter 1612 corresponds to a signal processing means according to the present invention, and the LD controller 1615 corresponds to a light source controlling means according to the present invention.

However, the present invention is not limited to the above embodiment, and may be implemented by a variety of embodiments. For example, the operation control unit 161 discussed above may be implemented by a hardware control circuit or by a computer unit. In addition, in the discussion above, the signal processing means according to the present invention is implemented by the low pass filter 1612; however, it may be implemented instead by a bandpass filter that cuts frequency components that exceed a prescribed upper limit and frequency components that fall below a prescribed lower limit. In this case, by passing through the bandpass filter, frequency components are extracted that correspond to the fluctuations in the intensity of the reflected light attributable to a deviation between the axis AXa and the center line of the cylindrical body 200, and frequency components that correspond to a defect in the inner circumferential surface 200a are not extracted; namely, the bandpass filter should be configured so that it can cut frequency components that correspond to those defects.

Figure 8:
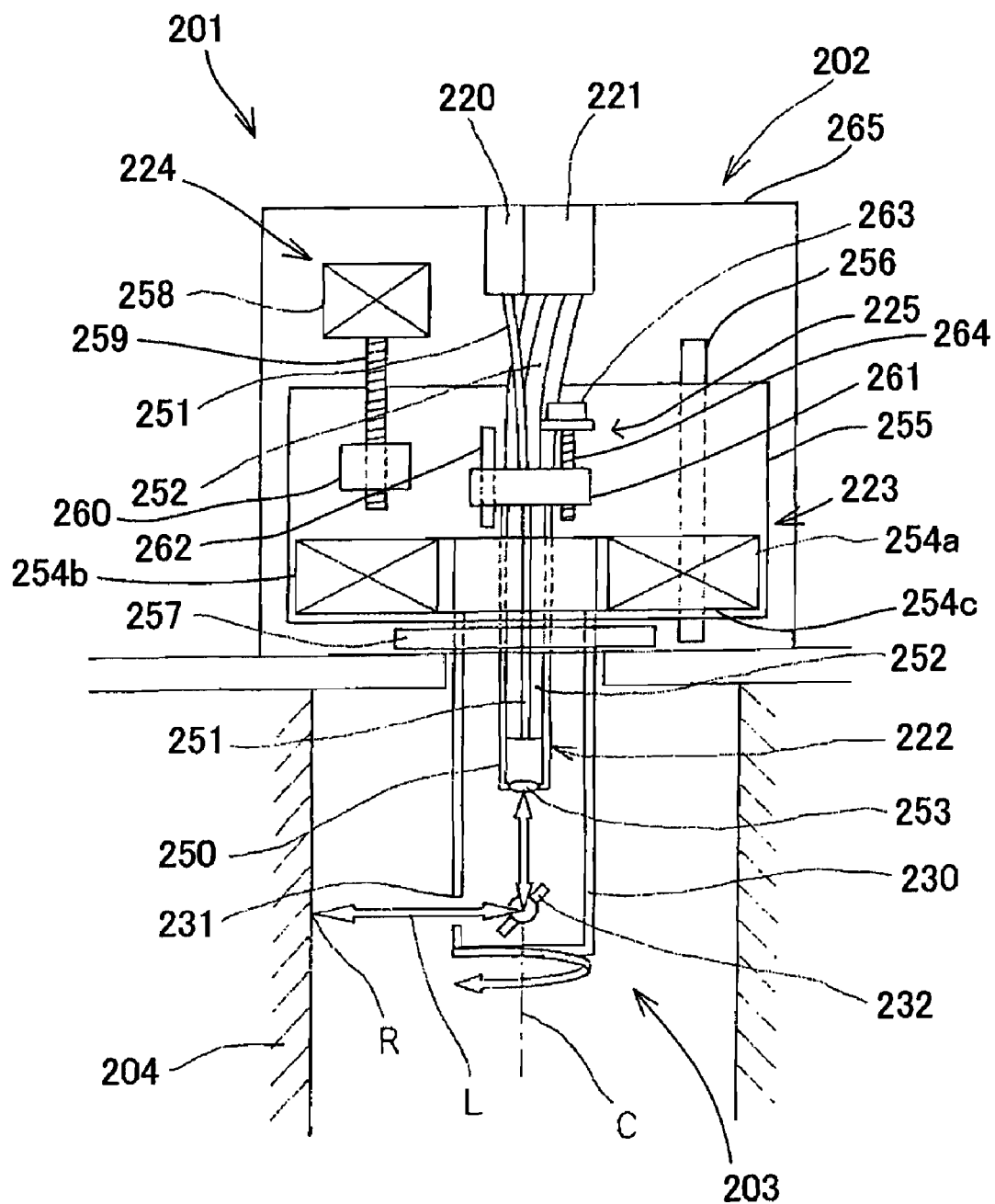
FIG. 8 is a schematic diagram of the surface inspection apparatus, wherein one embodiment of a head apparatus of the present invention is incorporated.

FIG. 8 shows one example of a surface inspection apparatus wherein one embodiment of a head apparatus of the present invention is integrated. A surface inspection apparatus 201 comprises a main body unit 202 and a head apparatus 203, which is provided so that it projects from the main body unit 202. The main body unit 202 comprises: a laser diode (hereinbelow, denoted LD) 220, which serves as the light source of the inspection light; a photodetector (hereinbelow, denoted PD) 221 that detects the reflected light of the inspection light irradiated on an inspection object 204; a light guide unit 222 that guides inspection light L, which is irradiated from the LD 220, in the projection direction of the head apparatus 203, and also guides the light reflected by the inspection object 204 that returns from the head apparatus 203 to a PD 221; a rotary mechanism 223 that rotates the head apparatus 203 around a rotational axis C, which extends in the projection direction thereof; a linear motion mechanism 224 that advances and retracts the head apparatus 203 along the directions of the rotational axis C; and a focal point adjusting mechanism 225 that focuses the inspection light by advancing and retracting the light guide unit 222 in the directions of the rotational axis C. The inspection object 204 is cylindrically shaped.

The light guide unit 222 comprises: a holding tube 250, which is disposed so that it is coaxial with the rotational axis C of the head apparatus 203; a lens 253, which is provided to the tip of the holding tube 250; a light projecting fiber 251, which guides the inspection light from the LD 220 to the lens 253; and a light receiving fiber 252, which guides the reflected light from the lens 253 to the PD 221. Furthermore, the light projecting fiber 251 is disposed so that it is coaxial with the rotational axis C, and a plurality of the light receiving fibers 252 may be disposed so that they surround the outer circumference of the light projecting fiber 251.

Figure 9:
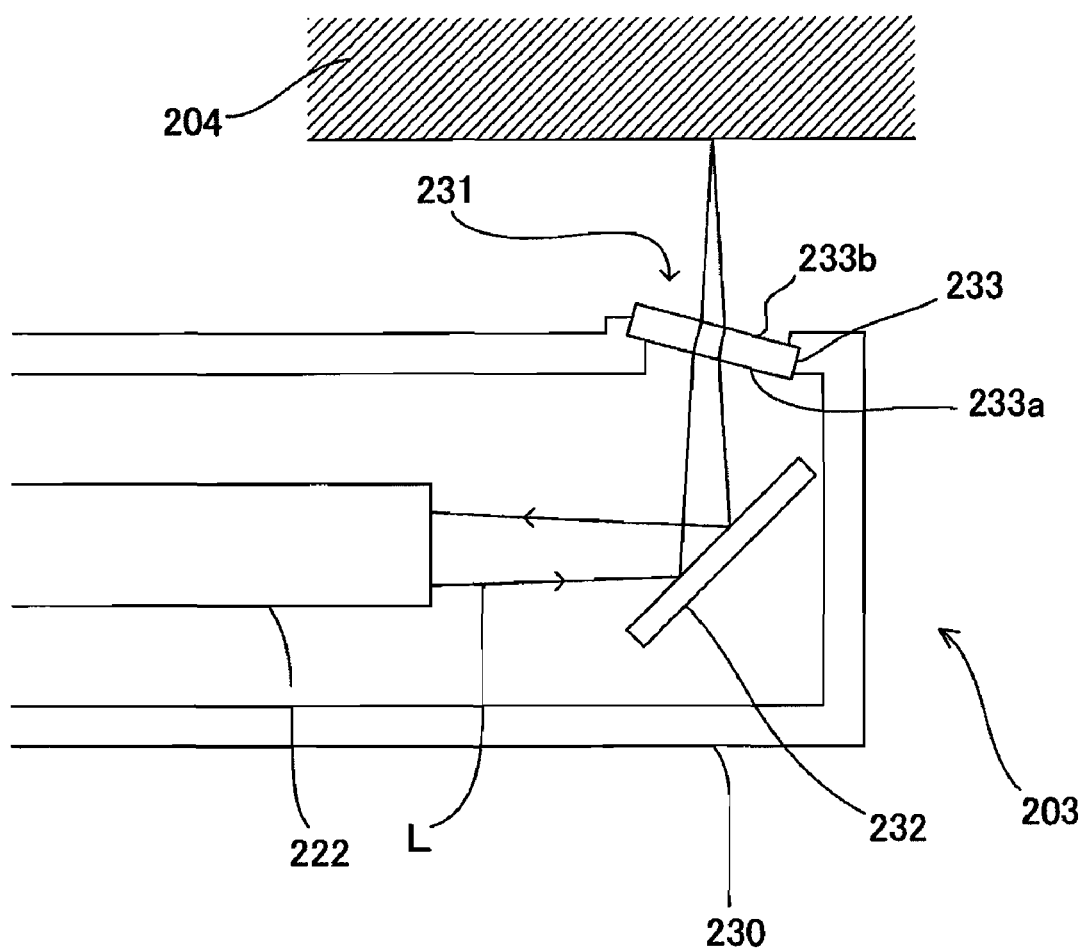
FIG. 9 is a schematic diagram that shows the configuration of one embodiment of the head apparatus.

As shown in detail in FIG. 9, the head apparatus 203 comprises: an outer tube 230, which serves as a head tube that is provided so that it is coaxial with and freely rotatable around the rotational axis C and wherein an opening 231 is formed at its outer circumference; and a protective window member 233, which is provided in the opening 231. The interior of the outer tube 230 is provided with a mirror 232, which serves as an optical path modifying means that modifies the optical path of the inspection light from the light guide unit 222 and the light reflected by the inspection object 204. The mirror 232 rotates integrally with the outer tube 230. With regard to the front and rear surfaces of the protective window member 233, the surface on the inner side of the outer tube 230 is a front surface 233a, and the surface on the outer side of the outer tube 230 is a rear surface 233b. The mirror 232 modifies the optical path of the inspection light L that emerges from the light guide unit 222 so that it leads toward the protective window member 233, causes the inspection light L to impinge the surface of the inspection object 204 through the protective window member 233, and modifies the optical path of the light that was reflected by the surface of the inspection object 204 and proceeded to the interior of the outer tube 230 through the protective window member 233 so that it leads toward the light guide unit 222.

The front surface 233a and the rear surface 233b of the protective window member 233 provided to the opening 231 of the outer tube 230 are parallel, and the protective window member 233 is installed so that the normal line directions of the front surface 233a and the rear surface 233b are equally inclined with respect to the direction in which the inspection light impinges the protective window member 233. The protective window member 233 is oriented so that the normal lines N of the front surface 233a and the rear surface 233b of the protective window member 233 are inclined toward the tip side of outer tube 230 as one goes toward the outer side of the head tube in the radial direction.

Returning to FIG. 8, the following explains the rotary mechanism 223, the linear motion mechanism 224, and the focal point adjusting mechanism 225. These three mechanisms have a relationship wherein the linear motion mechanism 224 moves a movable base 255—while the latter supports the rotary mechanism 223 and the focal point adjusting mechanism 225—by advancing and retracting it in the directions along the rotational axis C of the outer tube 230 with respect to a fixed base 265 of the main body unit 202.

The rotary mechanism 223 comprises: a pair of pulleys 254a, 254b, which are disposed so that they sandwich the base end part of the outer tube 230 rotatably supported on the movable base 255; a belt 254c, which is wound between the pulleys 254a, 254b; and a motor (not shown) that rotationally drives either of the pulleys 254a, 254b. The belt 254c is provided so that it contacts or engages with the base end part of the head tube 230. Accordingly, the motor rotates either of the pulleys 254a, 254b to drive the belt 254c, which rotationally drives the head tube 230 around the rotational axis C.

The linear motion mechanism 224 comprises: the movable base 255, which was discussed above; a guide 256, which is provided between the fixed base 265 and the movable base 255 of the main body unit 202 and guides the movable base 255 in the directions of the rotational axis C; a motor 258, which is attached to a fixed base 265 and serves as a drive source; and a feed screw 259, which is linked so that it is coaxial with an output shaft of the motor 258. The feed screw 259 is screwed into a nut 260, which is fixed to the movable base 255. Accordingly, by rotationally driving the feed screw 259 using the motor 258, the rotational drive of the motor 258 is converted to the linear motion of the movable base 255, which moves in the directions of the rotational axis C while being guided by the guide 256.

The focal point adjusting mechanism 225 comprises: a light guide unit holding member 261, which is provided on the movable base 255 and is attached to the base end part of the light guide unit 222; a guide 262, which is provided between the movable base 255 and the light guide unit holding member 261 that guides the light guide unit holding member 261 in the directions of the rotational axis C; a motor 263, which is attached to the movable base 255 and serves as a drive source; and a feed screw 264, which is linked so that it is coaxial with the output shaft of the motor 263. The feed screw 264 is screwed into the light guide unit holding member 261. Accordingly, by rotationally driving the feed screw 264 using the motor 263, the rotational drive of the motor 263 is converted to the linear motion of the light guide unit holding member 261, which moves in the directions of the rotational axis C while being guided by the guide 262. Thereby, the light guide unit 222 can move in the directions of the rotational axis C, and the inspection light and the reflected light can be focused by adjusting the position thereof.

The following explains the operation of the surface inspection apparatus 201. With the surface inspection apparatus 201 of the present embodiment, the rotary mechanism 223 rotationally drives the entire head apparatus 203 around the rotational axis C, and the linear motion mechanism 224 drives the head apparatus 203 in the directions of the rotational axis C and inserts it inside the inspection object 204. Synchronized with the rotational and linear motion of the head apparatus 203, the inspection light L radiates from the LD 220, travels through the light guide unit 222, and impinges the mirror 232, which directs the inspection light L in the radial direction of the head tube 230. That inspection light L irradiates the surface of the inspection object 204 through the protective window member 233. By these operations, the substantially entire inner surface of the inspection object 204 is scanned by the inspection light L. Furthermore, the light of the inspection light L that is reflected at the surface of the inspection object 204 passes through the protective window member 233 and reaches the mirror 232, which modifies its optical path so that it leads toward the light guide unit 222, after which it travels through the light guide unit 222 and then impinges the PD 221. Based on the intensity of the reflected light detected by the PD 221, surface defects and the like of the inspection object 204 are detected.

Figure 10:
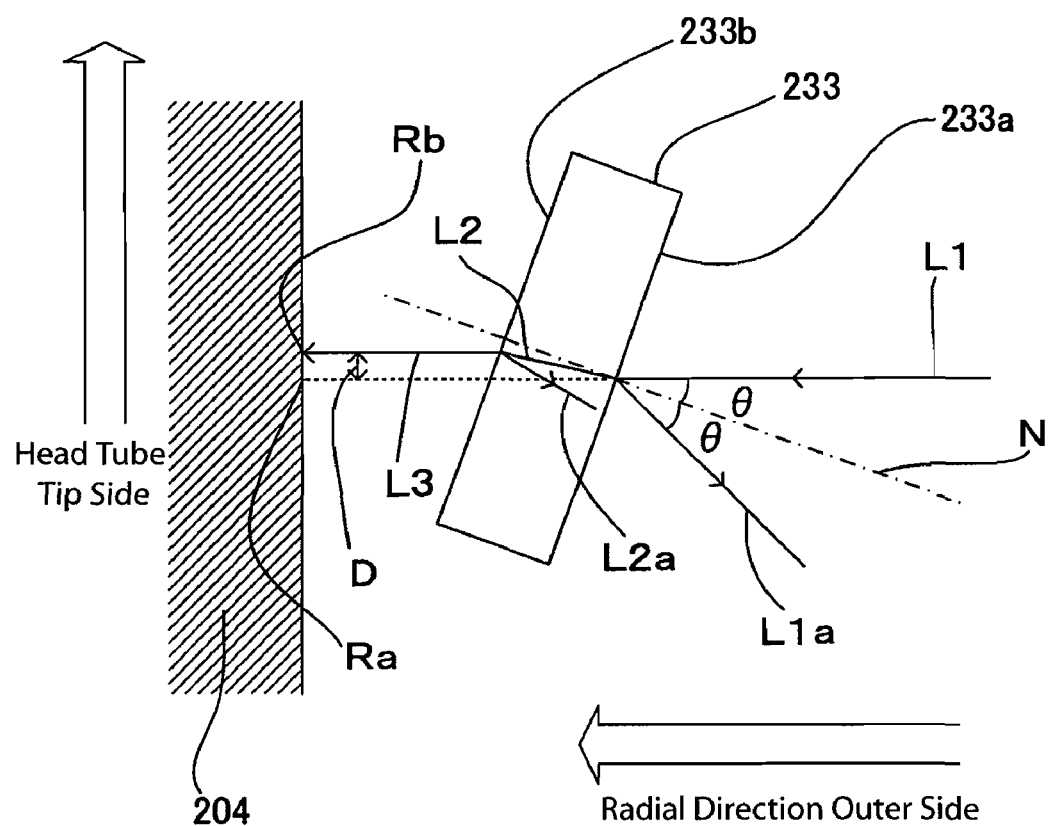

When inspection is performed as described above, the optical path of the inspection light L and the like in the head apparatus 203 is as shown in FIG. 10. In the head apparatus 203 of the present embodiment, the optical path of a light L1, which impinges the protective window member 233, and the normal lines N of the front surface 233a and the rear surface 233b of the protective window member 233 are equally inclined. If the light L1 impinges the front surface 233a of the protective window member 233 at an incidence angle θ, then a refracted light L2 and a reflected light L1a are generated. The light L1a reflects off the front surface 233a at the reflection angle θ, which causes it to deviate from the direction of the impinging light L1 and therefore it does not return in the direction of the light L1. Furthermore, when the light L2, which enters and is refracted inside the protective window member 233, reaches the rear surface 233b of the protective window member 233, it splits into a light L3, which refracts and emerges toward the inspection object 204, and a light L2a, which is reflected by the rear surface 233b. The light L2a also deviates once again from the direction of the impinging light L2 and does not return in the direction thereof.

The protective window member 233, which was discussed above, modifies the optical path of the light L1 that impinges the protective window member 233, and that light is projected to the inspection object 204 along the optical path of the light L3. As a result, the light L1 and the light L3 move in parallel, with the light L3 separated from the light L1 in the head tube tip side direction by a distance D, and an incidence position Rb of the inspection light on the inspection object 204 moves in the head tube tip side direction with respect to a position Ra, which is along an extension line of the light L1 optical path and intersects the surface of the inspection object 204.

Figure 11:
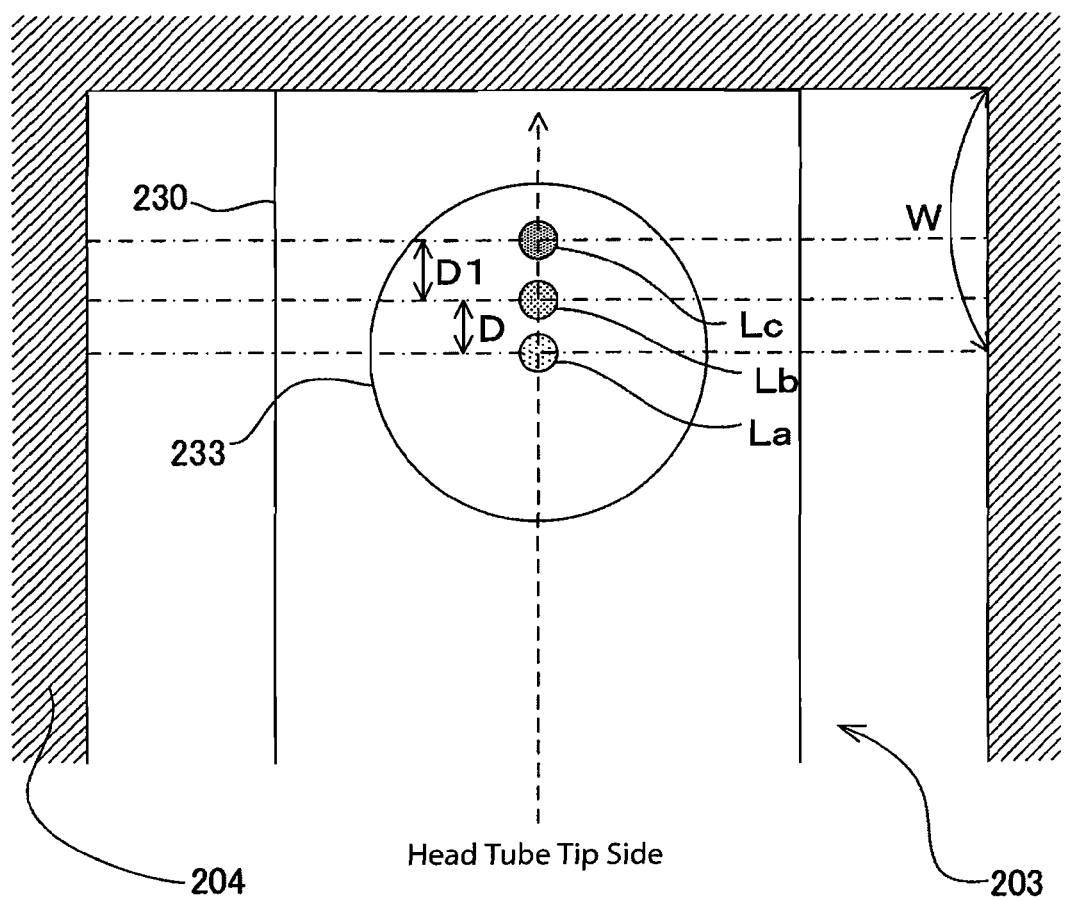
FIG. 11 shows the relationship between the head apparatus and the inspection object, viewed from the side of the inspection object onto which the inspection light is projected.

FIG. 11 shows the relationship between the head apparatus 203 and the inspection object 204, viewed from the side of the inspection object 204 whereto the inspection light is projected. In FIG. 11, the inspection object 204 is blind hole shaped. La is the light emergent position when the normal line directions of the front surfaces 233a, 233b of the protective window member 233 coincide with the light that impinges the protective window member 233, and Lb is the light emergent position when the normal line directions of the front surface 233a and the rear surface 233b of the protective window member 233 are substantially inclined. The emerging position Lb moves with respect to the conventional emerging position La by the distance D in the head tube 230 tip side direction. Furthermore, the emerging positions La, Lb correspond to the position Ra and the incidence position Rb, respectively, on the inspection object 204 shown in FIG. 10.

If the inspection object 204 is blind hole shaped, then inspection is not possible with the conventional art because the inspection light from the area that can be inspected by using the light from the emerging position La does not reach an area W on the head tube 230 tip side; however, by changing the emerging position to Lb, the dead angle decreases commensurately, and the inspection area widens in the amount of the distance D.

Furthermore, the above explained a preferred embodiment of the present invention based on the drawings, but the specific constitution is not limited to these embodiments, and it is understood that variations and modifications may be effected without departing from the spirit and scope of the invention. For example, the present embodiment explained a surface inspection head apparatus that inspects the inner surface of a cylindrically shaped or a blind hole shaped inspection object, but the present invention is not limited thereto, and may be adapted to the inspection of a surface of a planar inspection object.

Figure 12:
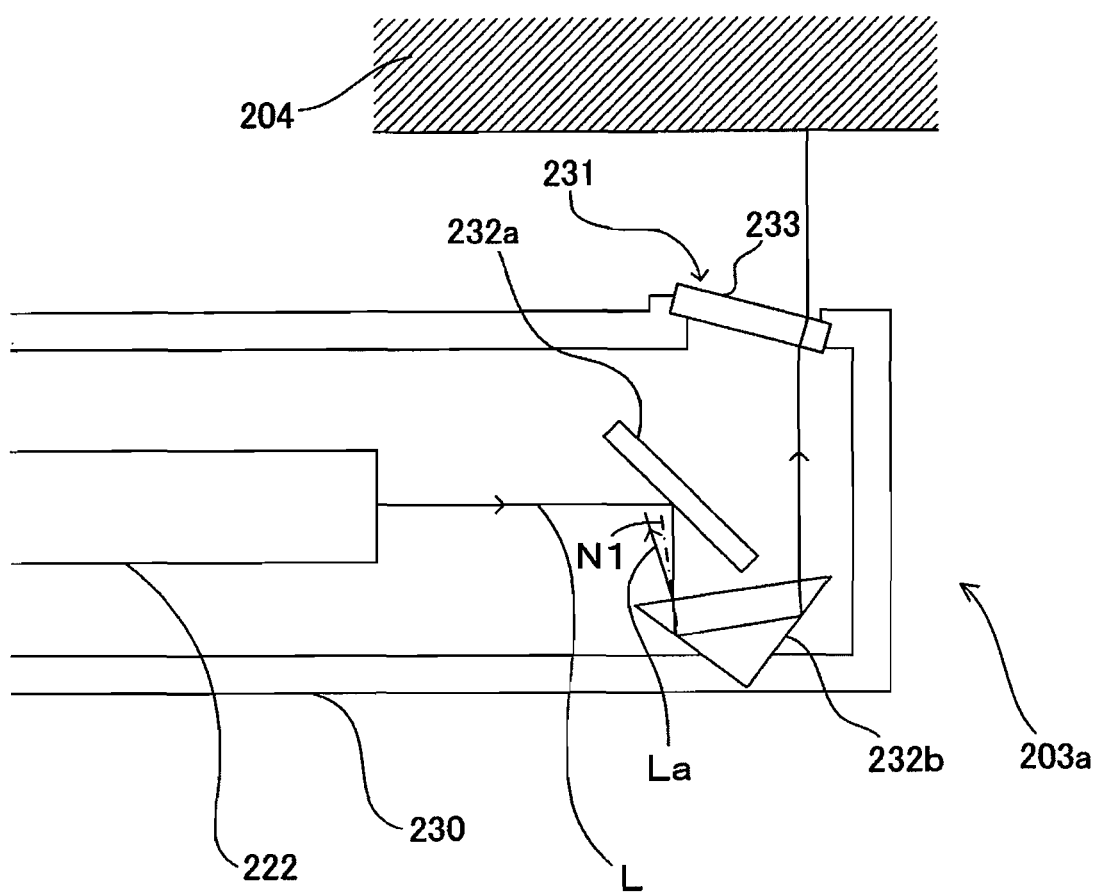
FIG. 12 is a schematic diagram of the head apparatus according to a modified example of the present invention.

FIG. 12 shows a modified example of the head apparatus of the present invention. Furthermore, parts that are common to those in FIG. 9 are assigned the identical symbols in FIG. 12 and the explanations thereof are omitted. A head apparatus 203a in the modified example comprises the outer tube 230 and the protective window member 233, which is provided in the opening 231; in addition, a mirror 232a and a prism 232b are provided inside the outer tube 230 and serve as optical path modifying means that modify the optical paths of the inspection light from the light guide unit 222 and the light reflected by the inspection object 204.

The mirror 232a modifies the optical path of the inspection light L that emerges from the light guide unit 222 so that it leads toward the prism 232b, and the prism 232b modifies the optical path of the inspection light from the mirror 232a so that it leads toward the protective window member 233. The prism 232b modifies the optical path of the reflected light, which is the inspection light that was reflected by the surface of the inspection object 204, that enters from the protective window member 233 so that the path leads toward the mirror 232a, which modifies the optical path of the light reflected by the prism 232b so that it leads toward the light guide unit 222.

The mirror 232a modifies the path of the impinging light at a substantially right angle. Furthermore, by twice modifying the optical path of the light from the mirror 232a at a substantially right angle within the same plane, that optical path further leads in the head tube 230 tip direction, and the inspection light emerges toward the protective window member 233. At that time, because a normal line N1 of the prism 232b is inclined with respect to the direction in which the inspection light L impinges the prism 232b, a deviation arises between the direction of the inspection light L and the direction of the reflected light L4 with respect to the inspection light L, and the reflected light La therefore does not return in the direction of the inspection light L.

FIG. 11 shows the emerging position of the present embodiment as an emerging position Lc. Compared with the emerging position Lb in the first embodiment of the head apparatus 203 of the present invention, the emerging position Lc in the present embodiment moves further in the amount of a distance D1 to the tip side of the head tube.

In addition, the present embodiment recited an example of using a mirror, a prism, and the like as the optical path modifying means 232; however, a plane mirror, a concave mirror, and the like may be used as the mirror, and a prism of an arbitrary shape, such as a rectangular prism, that conforms to design requirements may be used as the prism. Places in the text that gave explanations using a mirror and a prism are not necessarily limited thereto; for example, a prism may be used instead of a mirror, and a mirror may be used instead of a prism. The angles at which the optical path modifying means are attached are also not limited, provided that the optical path of the inspection light L from the light guide unit 222 is modified so that it leads toward the protective window member 233, and the optical path of the reflected light that passes through the protective window member 233 is modified so that it leads toward the light guide unit 222.

A light transmitting plate, such as a glass plate, an acrylic plate, or a plastic plate may be used as the protective window member 233.

The above embodiment explained a case wherein the front surface 233a and the rear surface 233b of the protective window member 233 are parallel and the normal line directions of the protective window member 233 are inclined— with respect to the direction in which the inspection light impinges the protective window member 233—toward the tip side as one goes toward the outer side of the head tube 230 in the radial direction; however, the front surface 233a and the rear surface 233b may be nonparallel, and the normal line directions of the front surface 233a and the rear surface 233b may both be inclined with respect to the direction in which the inspection light impinges the protective window member 233. Alternatively, the normal line direction of either the front surface 233a or the rear surface 233b may be inclined with respect to the direction in which the inspection light impinges the protective window member 233. The front surface 233a and the rear surface 233b may be parallel or nonparallel; in either case, the normal line direction of at least one of the front surface 233a and the rear surface 233b is not necessarily inclined—with respect to the direction in which the inspection light impinges the protective window member 233— toward the tip side as one goes to the outer side of the head tube 230 in the radial direction. In the present invention, the reflected light of at least one of the front surface 233a and the rear surface 233b deviates with respect to the direction in which the inspection light impinges the protective window member 233, and therefore it does not return in the direction of the light guide unit 222, which consequently makes it possible to perform high precision detection without unnecessary light components affecting the detected value.

According to the surface inspection apparatus described above, a second light receiving fiber group is disposed on the outer side of the first light receiving fiber group, and each of these fiber groups has a different positional relationship with the light projecting fiber, and consequently a single detecting means has a plurality of sensitivity characteristics that are different from one another. Accordingly, it is possible to produce a variety of sensitivity characteristics by appropriately using the signal of the first photoelectric converting means and the signal of the second photoelectric converting means in accordance with the type of the defect to be detected, or by combining these signals. In addition, because the intensity of the inspection light is controlled in accordance with the frequency components that correspond to fluctuations in the intensity of the reflected light attributable to a deviation between the rotational axis of the inspection head and the center line of the cylindrical body, it is possible to eliminate fluctuations in the reflected light intensity. Consequently, even if the rotational axis of the inspection head and the center line of the cylindrical body, which is the inspection object, are not made to coincide precisely, it is possible to obtain a two dimensional image without any periodic density variation. In addition, according to the above surface inspection head apparatus, it is possible to perform high precision detection even if a protective window member is provided. Accordingly, it is possible to incorporate the surface inspection head apparatus in a manufacturing line with tight inspection standards, such as in the manufacturing of automotive parts, and to use it to detect minute defects, which can improve inspection accuracy.

The invention claimed is:

1. A surface inspection apparatus that comprises: a light source that emits inspection light; an inspection head that is inserted inside a cylindrical body, which is an inspection object, that, while rotating around an axis of the cylindrical body and moving in the axial directions, projects the inspection light emitted from the light source to an inner circumferential surface of the cylindrical body and receives the light reflected thereby; and a photoelectric converting means that outputs a signal in accordance with the intensity of the reflected light received by the inspection head; and that generates a two dimensional image that corresponds to the inner circumferential surface based on the signal output by the photoelectric converting means; further comprising:

a signal processor extracting frequency components, which correspond to fluctuations in the intensity of the reflected light caused by a deviation between the axis and a center line of the cylindrical body, from the signal output by the photoelectric converting means; and a light source controller controlling the light source so that the intensity of the inspection light emitted from the light source varies with the differential between a prescribed reference value and the frequency components extracted by the signal processing means, wherein the signal processor extracting frequency components within a prescribed range that includes frequency components that correspond to the fluctuations and omits frequency components that correspond to a defect of the inner circumferential surface.

2. A surface inspection apparatus according to claim 1, wherein the light source controller controls the light source so that the intensity of the inspection light emitted from the light source is greater when the differential between the reference value and the frequency components is large than when it is small.

* * * * *